(12) United States Patent
Chauhan et al.

(10) Patent No.: US 12,337,005 B2
(45) Date of Patent: Jun. 24, 2025

(54) METHODS OF TREATING THROMBOSIS

(71) Applicant: UNIVERSITY OF IOWA RESEARCH FOUNDATION, Iowa City, IA (US)

(72) Inventors: Anil Chauhan, Iowa City, IA (US); Manasa K. Nayak, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

(21) Appl. No.: 17/331,366

(22) Filed: May 26, 2021

(65) Prior Publication Data

US 2021/0369742 A1    Dec. 2, 2021

Related U.S. Application Data

(60) Provisional application No. 63/030,084, filed on May 26, 2020.

(51) Int. Cl.
| | | |
|---|---|---|
| *A61K 31/63* | (2006.01) | |
| *A61K 31/5025* | (2006.01) | |
| *A61K 45/06* | (2006.01) | |
| *A61P 7/02* | (2006.01) | |

(52) U.S. Cl.
CPC .......... *A61K 31/63* (2013.01); *A61K 31/5025* (2013.01); *A61K 45/06* (2013.01); *A61P 7/02* (2018.01)

(58) Field of Classification Search
CPC .............. A61K 31/415; A61K 31/5025; A61K 31/519; A61K 31/551; A61K 31/63; A61K 45/06; A61P 7/02
See application file for complete search history.

(56) References Cited

U.S. PATENT DOCUMENTS

2009/0163545 A1   6/2009  Goldfarb
2017/0105998 A1*  4/2017  Goldman ............... A61K 45/06

FOREIGN PATENT DOCUMENTS

| WO | 2010042867 A2 | 4/2010 |
| WO | 2012151450 A1 | 11/2012 |
| WO | 2013056153 A1 | 4/2013 |
| WO | 2019075367 A1 | 4/2019 |

OTHER PUBLICATIONS

Dhanesha et al. Stroke, Jan. 30, 2019, 50:ATMP25 (Year: 2019).*
Boxer, M , et al., "Evaluation of Substituted N, N0-Diarylsulfonamides as Activators of the Tumor Cell Specific M2 Isoform of Pyruvate Kinase", J Med Chem 53, 1048-1055 (2010).
Chaneton, B , et al., "Serine is a natural ligand and allosteric activator of pyruvate kinase M2", Nature 491, 458-462 (2012).
Jiang, J , et al., "Evaluation of thieno[3,2-b]pyrrole[3,2-d]pyridazinones as activators of the tumor cell specific M2 soform of pyruvate kinase", Bioorganic & Medicinal Chemistry Letters 20, 3387-3393 (2010).
Matsui, Y , et al., "Discovery and structure-guided fragment-linking of 4-(2,3-dichlorobenzoyl)-1-methyl-pyrrole-2-carboxamide as a pyruvate kinase M2 activator", Bioorganic & Medicinal Chemistry 25, 3540-3546 (2017).
Nayak, M , et al., "Manipulating Metabolic Plasticity By Targeting Pyruvate Kinase M2 in Platelets Inhibits Arterial Thrombosis", Blood 132 (Supplement 1), 868 (2018).
Nayak, M , et al., "Targeting Metabolic Enzyme Pyruvate Kinase M2: A Novel Strategy to Inhibit Platelet Function and Arterial Thrombosis", Blood 134 (Supplement 1), 1056 (2019).
Nayak, M , et al., "The metabolic enzyme pyruvate kinase M2 regulates platelet function and arterial thrombosis", Blood 137 (12), 1658-1668 (2021).
Walsh, M , et al., "2-Oxo-N-aryl-1,2,3,4-tetrahydroquinoline-6-sulfonamides as activators of the tumor cell specific M2 soform of pyruvate kinase", Bioorganic & Medicinal Chemistry Letters 21, 6322-6327 (2011).
Zhang, Y , et al., "New pyridin-3-ylmethyl carbamodithioic esters activate pyruvate kinase M2 and potential anticancer lead compounds", Bioorganic & Medicinal Chemistry 23, 4815-4823 (2015).
Cheng, X. , et al., "Prothrombotic effects of high uric acid in mice via activation of MEF2C-dependent NF-κB pathway by upregulating let-7c", Aging 12(18), 17976-17989 (2020).
Crea, F. , "Thrombotic and bleeding complications during antithrombotic treatment: the need for new therapeutic targets", Eur Heart J. 44(20), 1767-1770 (2023).
Dhanesha, N. , et al., "Treatment with Uric Acid Reduces Infarct and Improves Neurologic Function in Female Mice After Transient Cerebral Ischemia", Journal of Stroke and Cerebrovascular Diseases, https://doi.org/10.1016/j.jstrokecerebrovasdis.2017.12.043, 27(5), 1412-1416 (2018).
Escaned, J. , et al., "Ticagrelor monotherapy in patients at high bleeding risk undergoing percutaneous coronary intervention: TWILIGHT-HBR", Eur Heart J 42(45), 4624-4634 (2021).
Kimura, Y. , et al., "Soluble Uric Acid Promotes Atherosclerosis via AMPK (AMP-Activated Protein Kinase)-Mediated Inflammation", Arterioscler Thromb Vasc Biol 40(3), 570-582 (2020).
Kwok, C. , et al., "Percutaneous coronary intervention in patients with cancer and readmissions within 90 days for acute myocardial infarction and bleeding in the USA", Eur Heart J. 42(10), 1019-1034 (2021).
Lees, K. , et al., "NXY-059 for acute ischemic stroke", N Engl J Med 354(6), 588-600 (2006).
Meyre, P , et al., "Bleeding and ischaemic events after first bleed in anticoagulated atrial fibrillation patients: risk and timing", Eur Heart J 43(47), 4899-4908 (2022).

(Continued)

*Primary Examiner* — Kara R. McMillian
(74) *Attorney, Agent, or Firm* — Viksnins Harris Padys Malen LLP

(57) ABSTRACT

The present invention provides in certain embodiments methods of inhibiting platelet function or thrombosis, inhibiting pyruvate kinase M2 (PKM2) dimerization, and/or treating a disease associated with thrombosis by administering a composition comprising a dimeric pyruvate kinase M2 (PKM2) inhibitor in a patient in need thereof.

5 Claims, 14 Drawing Sheets
(11 of 14 Drawing Sheet(s) Filed in Color)

(56) References Cited

OTHER PUBLICATIONS

Nilsson, D., et al., "NXY-059 does not affect bleeding time in healthy volunteers: a randomized, double-blind, placebo-controlled, 3-period crossover phase I study", J Clin Pharmacol 47(2), 264-272 (2007).

Oyama, K., et al., "Serial assessment of biomarkers and the risk of stroke or systemic embolism and bleeding in patients with atrial fibrillation in the ENGAGE AF-TIMI 48 trial", Eur Heart J. 42(17), 1698-1706 (2021).

Valgimigli, M., et al., "Duration of antiplatelet therapy after complex percutaneous coronary intervention in patients at high bleeding risk: a MASTER DAPT trial sub-analysis", European Heart Journal 43(33), 3100-3114 (2022).

Yang, Q., et al., "LDL cholesterol levels and in-hospital bleeding in patients on high-intensity antithrombotic therapy: findings from the CCC-ACS project", Eur Heart J. 42(33), 3175-3186 (2021).

Zhang, J., et al., "Low-dose rivaroxaban plus aspirin for elderly patients with symptomatic peripheral artery disease: is it worth the bleeding risk?", Eur Heart J. 42(39), 4049-4052 (2021).

Clausen, B., et al., "Conditional gene targeting in macrophages and granulocytes using LysMcre mice", Transgenic Research 8, 265-277 (1999).

Dayton, T, et al., "Germline loss of PKM2 promotes metabolic distress and hepatocellular carcinoma", Genes & Development 30, 1020-1033 (2016).

Grover, S., et al., "Intrinsic Pathway of Coagulation and Thrombosis Insights From Animal Models", Arterioscler Thromb Vasc Biol 39, 331-338 (2019).

Iba, T., et al., "Inflammation and thrombosis: roles of neutrophils, platelets and endothelial cells and their interactions in thrombus formation during sepsis", Journal of Thrombosis and Haemostasis 16, 231-241 (2018).

Jiang, J, et al., "ML265: A potent PKM2 activator induces tetramerization and reduces tumor formation and size in a mouse xenograft model", Probe Reports from the NIH Molecular Libraries Program, PubChem Summary Bioassay Identifier (AID): 602359, 19 pages (2012).

Swystun, L., et al., "The role of leukocytes in thrombosis", Blood 128 (6), 753-762 (2016).

Tiedt, R., et al., "Pf4-Cre transgenic mice allow the generation of lineage-restricted gene knockouts for studying megakaryocyte and platelet function in vivo", Blood 109 (4), 1503-1506 (2007).

Xie, M, et al., "PKM2-dependent glycolysis promotes NLRP3 and AIM2 inflammasome activation", Nature Communications 7, 13280, 1-13 (2016).

Yau, J, et al., "Endothelial cell control of thrombosis", BMC Cardiovascular Disorders 15, 130, 11 pages (2015).

* cited by examiner

Figures 1A-1D
A
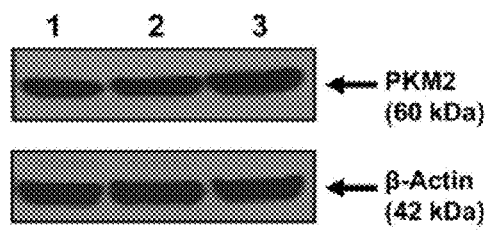
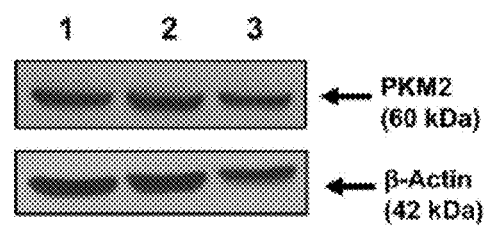
B
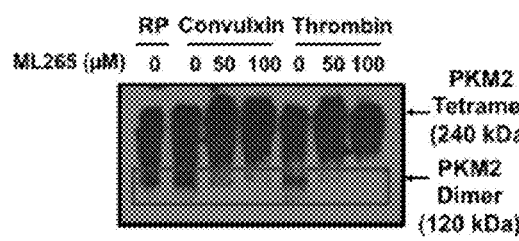
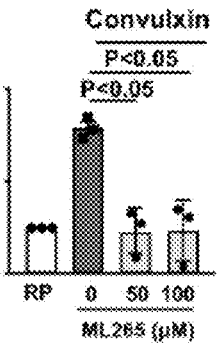
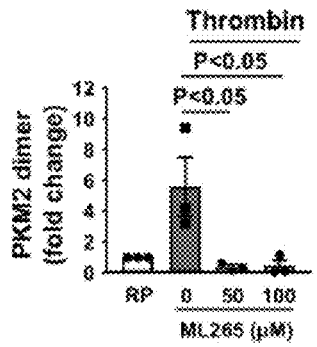
C
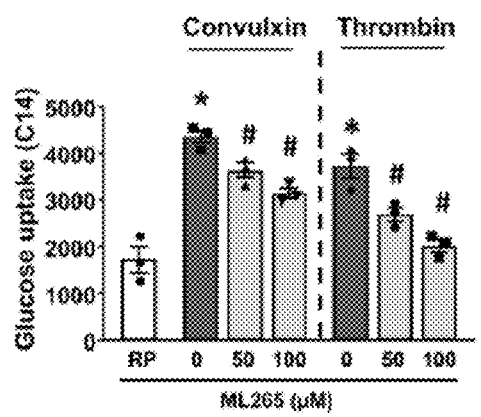
D
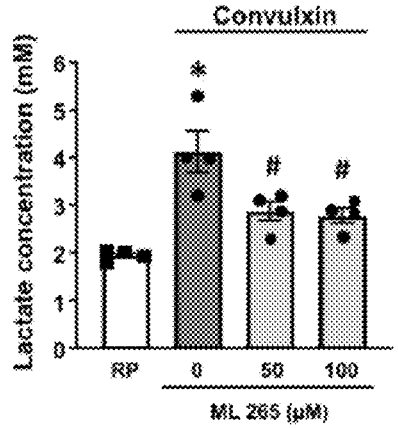

Figures 11A-11B
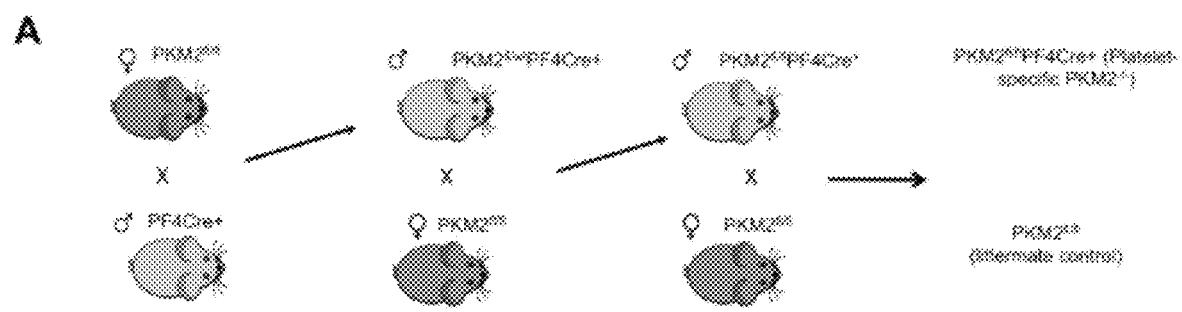
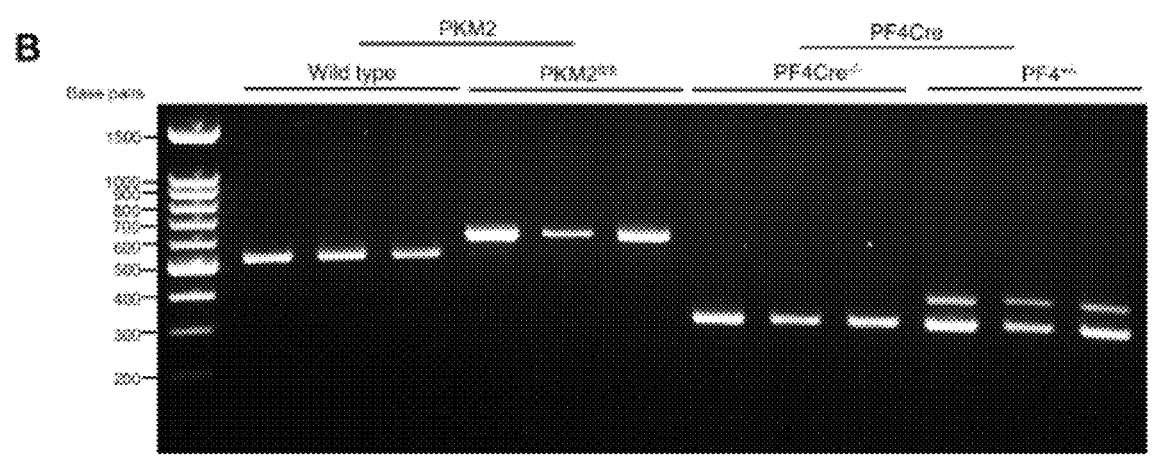
Figure 12
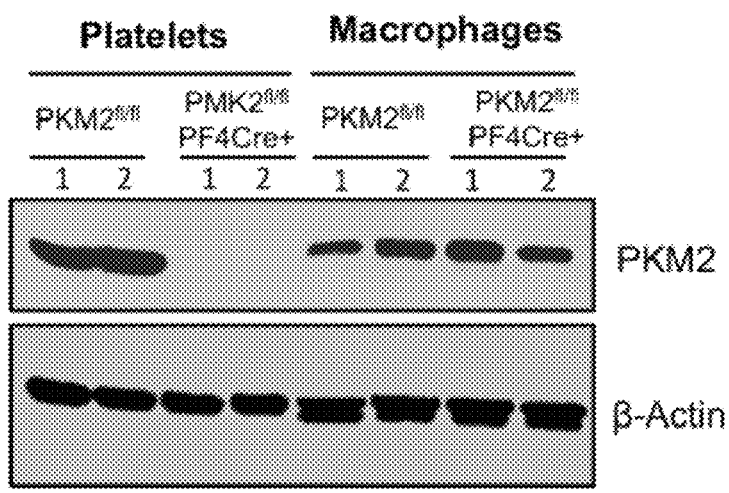

METHODS OF TREATING THROMBOSIS

RELATED APPLICATION

This application claims priority to U.S. Provisional Application No. 63/030,084 that was filed on May 26, 2020. The content of the application referenced above is herein incorporated by reference in its entirety.

STATEMENT REGARDING FEDERALLY SPONSORED RESEARCH

This invention was made with government support under HL139926 awarded by National Institutes of Health. The government has certain rights in the invention.

BACKGROUND

Acute coronary syndromes and stroke are leading causes of mortality and morbidity and result in immense health and economic burden. Current strategies to prevent acute coronary syndromes and ischemic stroke in at-risk patients rely on antiplatelet drugs (e.g., aspirin and P2Y12 inhibitors), which do not translate into clinical efficacy in one-third of patients. More potent anti-platelet agents such as glycoprotein IIbIIIa inhibitors (e.g., abciximab) are associated with bleeding complications and are not suitable for long-term use. Understanding the cellular mechanism that regulate platelet activation and thrombosis is, therefore, of considerable importance. Thus, there is a critical and unmet need for new therapeutic interventions that can inhibit platelet function or arterial thrombosis, with minimal bleeding risk. Herein, we report a novel anti-platelet strategy to limit pyruvate kinase M2 (PKM2) dimerization, and/or treating a disease associated with thrombosis by administering a small molecule that limits pyruvate kinase M2 (PKM2) dimerization in a patient in need thereof.

SUMMARY

Very little is known about the role of metabolic regulatory mechanisms in platelet activation and thrombosis. Comprehensive metabolomic analysis of human platelets revealed that the glycolytic enzyme pyruvate kinase M2 (PKM2) regulates glycerophospholipids and arachidonic acid metabolism, which are known to contribute to platelet activation. Limiting PKM2 dimer formation reduced platelet activation, aggregation, clot retraction, and thrombus formation under arterial shear stress in vitro in both human and murine platelets, and downregulated PI3 kinase-mediated Akt/GSK3 signaling in platelets. Murine studies using platelet-specific PKM2-deficient mice confirmed a mechanistic role for PKM2 in regulating platelet function and arterial thrombosis. These findings reveal a major role for PKM2 in coordinating multiple aspects of platelet function from metabolic plasticity to cellular signaling to thrombosis and a potential target for antithrombotic therapeutic intervention.

The present invention provides in certain embodiments a method of inhibiting platelet function or thrombosis by administering a composition comprising an inhibitor of dimeric pyruvate kinase M2 (PKM2) or an activator/stabilizer of tetramer PKM2 in a patient in need thereof. PKM2 exists in two forms: dimer and tetramer. PKM2 dimer inhibitor inhibits free PKM2 dimers, and activates or stabilizes tetrameric PKM2 by binding to the dimer-dimer interface between two subunits of PKM2 and inducing or stabilizing tetramerization.

The present invention provides in certain embodiments a method of inhibiting pyruvate kinase M2 (PKM2) dimerization by administering a dimeric PKM2 inhibitor or an activator/stabilizer of tetramer PKM2 in a patient in need thereof.

The present invention provides in certain embodiments a method of treating a disease associated with thrombosis by administering an inhibitor of dimeric pyruvate kinase M2 (PKM2) or an activator/stabilizer of tetramer PKM2 in a patient in need thereof.

As used herein an "inhibitor of PKM2" inhibits PKM2 dimerization. In certain embodiments, the PKM2 inhibitor is a member of the thieno[3,2-b]pyrrole[3,2-d]pyridazinones class, such as ML265 or TEPP-46 or CID-44246499 or NCGC00186528. In certain embodiments, the PKM2 inhibitor is a member of the thieno[3,2-b]pyrrole[3,2-d]pyridazinones substituted N,N'-diarylsulfonamides, such as a series of N,N0-diarylsulfonamides, 2-Oxo-N-aryl-1,2,3,4-tetrahydroquinoline-6-sulfonamides. In certain embodiments, the PKM2 inhibitor is a member of the 3-(trifluoromethyl)-1H-pyrazole-5-carboxamide class. In certain embodiments, the PKM2 inhibitor is 3-[[4-(2,3-dihydro-1,4-benzodioxin-6-ylsulfonyl)-1,4-diazepan-1-yl]sulfonyl]aniline (DASA). (Zhang et al., New pyridine-3-ylmethyl carbamodithioic esters activate pyruvate kinase M2 and potential anticancer lead compounds, *Bioorganic & Medicinal Chemistry* 23 (2015) 4815-4823.)

In certain embodiments, the inhibitor of PKM2 is ML265.

As used herein an "activator/stabilizer of tetramer PKM2" activates or stabilizes tetrameric PKM2. In certain embodiments, activator/stabilizer of tetramer PKM2 is N,N0-diarylsulfonamides; thieno[3,2-b]pyrrole[3,2-d]pyridazinones; 2-oxo-N-aryl-1,2,3,4-tetrahydroquinoline-6-sulfonamides; quinolone sulfonamides; 1-(sulfonyl)-5-(arylsulfonyl)indoline; 2-((1H-benzo[d]imida-zol-1-yl)methyl)-4H-pyrido[1,2-a]pyrimidin-4-ones; or 3-(trifluoromethyl)-1H-pyrazole-5-carboxamide.

BRIEF DESCRIPTION OF DRAWINGS

The patent or application file contains at least one drawing executed in color. Copies of this patent or patent application publication with color drawings will be provided by the Office upon request and payment of the necessary fee.

FIGS. 1A-1F. (A) Western blot of PKM2 in human and murine platelets. (B) The left panel shows representative image of the Western blot, non-reducing (native), of PKM2 dimer and tetramer expression in human platelets pre-treated with vehicle or ML265 and stimulated with convulxin (100 ng/ml) or thrombin (0.1 U/mL). The middle and right panels show densitometry analysis of Western blot. Red box denotes the PKM2 dimers. Values are mean±SEM, n=3 individual donors/group. *P<0.05 vs control. One-way ANOVA followed by Tukey's multiple comparisons test. (C and D) Effect of PKM2 inhibition on glucose uptake and lactate production in human platelets with convulxin (100 ng/ml) or thrombin (0.1 U/ml). Values are mean±SEM, n=3-4 individual donors/group. *P<0.05 vs. resting platelets; #P<0.05 vs. activated platelets (vehicle). Two-way ANOVA followed by Tukey's multiple comparisons test. (E) Heatmaps of hierarchically clustered metabolites in human platelets pretreated with vehicle or ML265 and stimulated with convulxin (100 ng/ml). Metabolites enrichment analysis of glycolytic, glycerophospholipid, and arachidonate metabolism. Columns represent individual groups, and rows represent metabolites. n=5 individual donors/group. Welch's two-sample t-test. (F) Effect of dimeric PKM2 inhibition on thromboxane A2 production in stimulated-platelets with convulxin (5 ng/ml; upper panel) and thrombin (0.02 U/ml; lower panel). Values are mean±SEM, n=3 individual donors/group. One-way ANOVA followed by Tukey's multiple comparisons test.

FIG. 2. Dimeric PKM2 regulates multiple aspects of platelet function in human platelets. (A) Human platelet-rich plasma pretreated with vehicle or ML265 and stimulated with convulxin (5 ng/ml), collagen (2.5 µg), TRAP (10 µM) and ADP (5 µM). Results are expressed as the percentage change in light transmission with respect to the blank (platelet-poor plasma/buffer without platelets), set at 100%. The upper panel in each bar graph denotes the representative aggregation curves (blue: vehicle-control; black: 50 µM ML265; red: 100 µM ML265). Values are mean±SEM, n=5 individual donors/group. One-way ANOVA followed by Tukey's multiple comparisons test. (B, C and D) Effect of dimeric PKM2 inhibition on integrin αIIbβ3 activation, P-selectin exposure, and ATP secretion from dense granules in stimulated-platelets with convulxin (5 ng/ml), TRAP (50 µM) and thrombin (0.1 U/mL). Values are mean±SEM, n=4-5 individual donors/group. *P<0.05 vs. resting platelets, #P<0.05 vs. vehicle. Two-way ANOVA (B & C) and One-way ANOVA (D) with Tukey's multiple comparisons. (E) Clot retraction was measured for 1 hr in platelet-rich plasma, supplemented with RBC, after adding 0.25 U/ml thrombin in the presence of a vehicle or ML265 (50 and 100 µM). The left panels show representative images at different time points. The right panel shows the quantification of clot size with time. Values are mean±SEM, n=4 individual donors/group. Two-way ANOVA with Tukey's multiple comparison test. (F) Human whole blood pretreated with vehicle or ML265 (150 µM) was perfused over a collagen coated (100 µg/mL) surface for 5 minutes at a shear rate of $1500\ s_{-1}$ in a flow chamber system from Bioflux Microfluidics. The left panel shows the representative image at the end of the assay. The middle panel shows the thrombus growth on collagen matrix over time. Slopes over time showed that the rate of thrombus growth in ML265 treated whole blood (slope: 37.92) was decreased when compared with vehicle control (slope: 237.3). Values are mean±SEM, with n=3 individual donors/group. * indicates P<0.05. Two-way ANOVA with Tukey's multiple comparison test. The right panel shows the surface area covered by fluorescent platelets after 5 minutes of perfusion. 3 to 4 areas from different areas of the flow chamber were analyzed from each blood sample, Values are mean±SEM, with n=11 areas/group. Mann-Whitney test.

FIGS. 11A-11B. Generation of platelet-specific PKM2 deficient mice. (A) Schematic showing the strategy to generate PKM2$_{fl/fl}$PF4Cre+ deficient mice. (B) Genomic PCR confirming the presence of PF4Cre+ gene in PKM2$_{fl/fl}$ mice. n=3/group.

FIG. 12. Confirmation of lack of PKM2 in platelets. Western blot confirming the specific deletion of PKM2 from platelets, but not peritoneal monocytes/macrophages. 1 and 2 are samples from individual mouse.

DETAILED DESCRIPTION

Figures 1E, 1F:
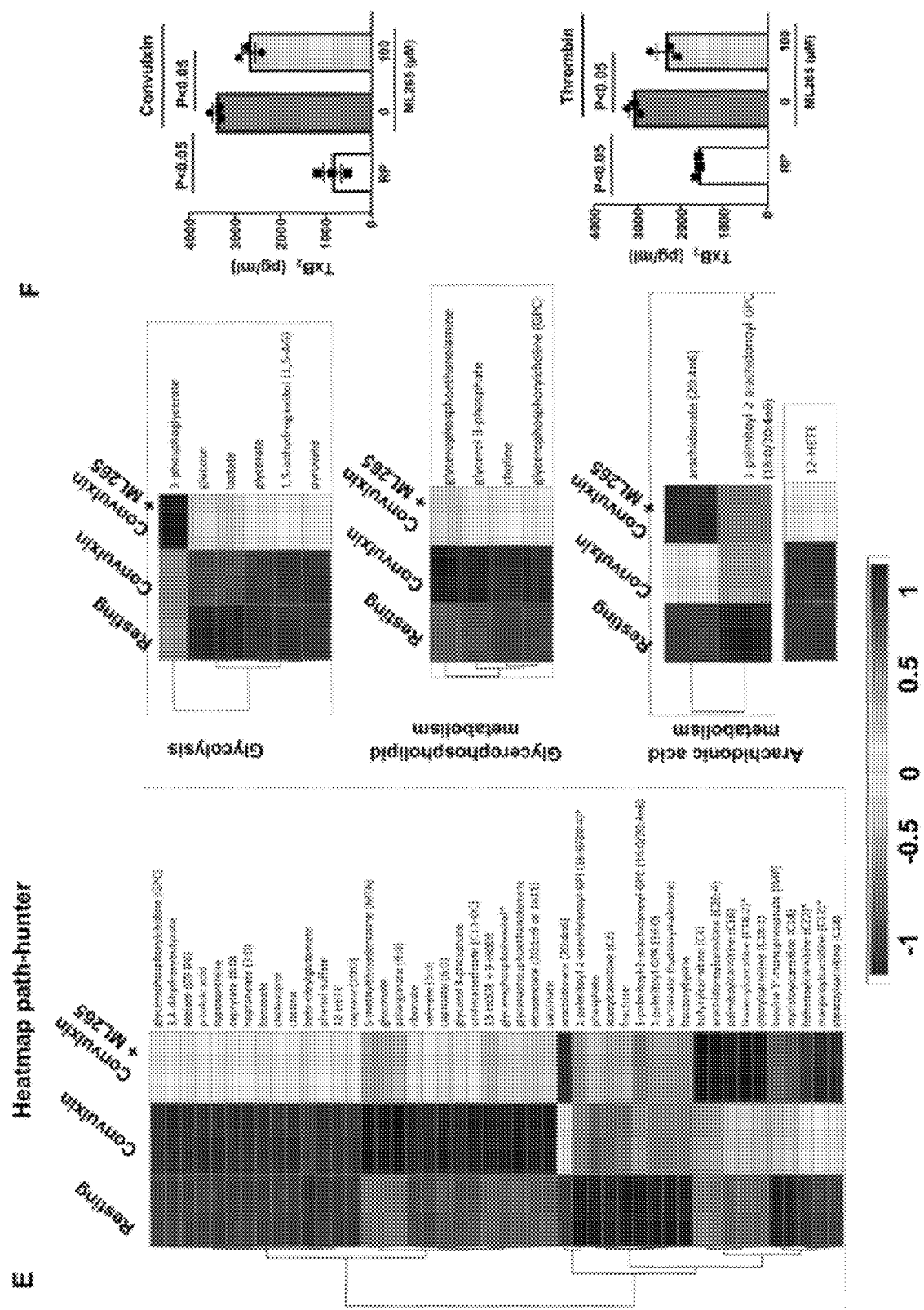

Current anti-thrombotic therapies either target proteins in the coagulation pathway or major platelet adhesion receptors, but are associated with increased risk of bleeding that limits their long-term use. Evidence suggests that metabolic plasticity exists in platelets that facilitates the transition of platelets from resting to an activated state. Herein, a novel anti-thrombotic strategy is reported that targets metabolic plasticity in platelets via modulating metabolic enzyme, Pyruvate Kinase M2 (PKM2). Using multiple agonist-induced and microfluidic assays, it is shown that a small molecule ML265 (an inhibitor of PKM2) inhibits both human and mouse platelet function via glycolytic (by reducing glucose uptake and lactate production) and non-glycolytic (by negatively regulating PI3 kinase-mediated Akt and GSK3 signaling) pathways. A comprehensive metabolomics investigation on human platelets revealed that targeting PKM2 downregulates platelets metabolism including glycerophospholipids and arachidonic acid pathways. Platelet-specific PKM2 deficient mice exhibited impaired agonist-induced platelet activation, aggregation, clot retraction and less susceptibility to arterial thrombosis, without altering hemostasis. Wild-type mice treated with ML265 were less susceptible to arterial thrombosis with unaltered tail bleeding time. These findings reveal a novel mechanistic link between metabolic enzyme PKM2, platelet function and thrombosis that is useful as a potent antithrombotic strategy.

Methods of Treatment

In certain embodiments, the present invention provides a method of inhibiting platelet function or thrombosis by administering a composition comprising a pyruvate kinase M2 (PKM2) inhibitor in a patient in need thereof. The present invention provides in certain embodiments a method of treating a disease associated with thrombosis by administering an inhibitor of dimeric pyruvate kinase M2 (PKM2) or an activator/stabilizer of tetramer PKM2 in a patient in need thereof.

As used herein an "inhibitor of PKM2" inhibits PKM2 dimerization. In certain embodiments, the PKM2 inhibitor is a member of the thieno[3,2-b]pyrrole[3,2-d]pyridazinones class (Jiang et al., Evaluation of thieno[3,2-b]pyrrole[3,2-d] pyridazinones as activators of the tumor cell specific M2 isoform of pyruvate kinase, Bioorganic & Med. Chem Lett. 20 (2010) 3387-3393), such as ML265 (6-[(3-aminophenyl) methyl]-4,6-dihydro-4-methyl-2-(methylsulfinyl)-5H-thieno[2',3':4,5]pyrrolo[2,3-d]pyridazine-5-one) or TEPP-46 or CID-44246499 or NCGC00186528. In certain embodiments, the PKM2 inhibitor is a member of the thieno[3,2-b]pyrrole[3,2-d]pyridazinones substituted N,N'-diarylsulfonamides, such as a series of N,N0-diarylsulfonamides, 2-Oxo-N-aryl-1,2,3,4-tetrahydroquinoline-6-sulfonamides. In certain embodiments, the PKM2 inhibitor is a member of the 3-(trifluoromethyl)-1H-pyrazole-5-carboxamide class. Xu et al., Discovery of 3-(trifluoromethyl)-1H-pyrazole-5-carboxamide activators of the M2 isoform of pyruvate kinase (PKM2), Bioorg. & Med Chem Lett. 24 (2014) 515-519. In certain embodiments, the PKM2 inhibitor is 3-[[4-(2,3-dihydro-1,4-benzodioxin-6-ylsulfonyl)-1,4-diazepan-1-yl]sulfonyl]aniline (DASA).

As used herein an "activator/stabilizer of tetramer PKM2" activates or stabilizes tetrameric PKM2. (Anastasiou et al., Pyruvate kinase M2 activators promote tetramer formation and suppress tumorigenesis, Nature Chem. Bio. 8, 839-847 (2012); Thomas et al., WO 2010/042867 (2010 Feb. 15); Ling et al., CN104370936 (2015 Feb. 25); Gdynia et al., WO 2017/098051; Siddiqui-Jain et al, WO 2019/075367 (2019 Apr. 18); Su, WO 2012/151450 (2012 Nov. 8); Kung, WO 2013/056153; Walsh et al., 2-oxo-N-aryl-1,2,3,4-tetrahydroquinoline-6-sulfonamides as activators of the tumor cell specific M2 isoform of pyruvate kinase, Bioorg & Med. Chem Lett. 21 (2011) 6322-6327; Boxer et al., Evaluation of substituted N—N'-diarylsulfonamides as activators of the tumor cell specific M2 isoform of pyruvate kinase, J. Med. Chem. 2010, 53, 1048-1055; Chaneton et al., Serine is a natural ligand and allosteric activator of pyruvate kinase M2, Nature 491 (2012) 458-462). In certain embodiments, activator/stabilizer of tetramer PKM2 is N,N0-diarylsulfonamides; thieno[3,2-b]pyrrole[3,2-d]pyridazinones; 2-oxo-N-aryl-1,2,3,4-tetrahy-droquinoline-6-sulfonamides; quinolone sulfonamides; 1-(sulfonyl)-5-(arylsulfonyl)indoline; 2-((1H-benzo[d]imida-zol-1-yl)methyl)-4H-pyrido[1,2-a] pyrimidin-4-ones; or 3-(trifluoromethyl)-1H-pyrazole-5-carboxamide.

In certain embodiments, the platelet function or thrombosis is inhibited by the PKM2 inhibitor by about 10 to 100% as compared to pre-treatment function. In certain embodiments, the platelet function or thrombosis is inhibited by 10%, 20%, 30%, 40%, 50%, 60%, 70%, 80%, 90% or 100%.

In certain embodiments, the inhibition does not alter hemostasis. As used herein, hemostasis is a process to prevent and stop bleeding. It is the innate response for the body to stop bleeding and loss of blood. Current antithrombotic drugs, including widely used antiplatelet agents and anticoagulants, are associated with significant bleeding risk or having an altered or changed or disturbed hemostasis. On the contrary, our inhibitor of PKM2 dimer (stabilizer of PKM2 tetramer) is found to be a good anti-platelet and anti-thrombotic agent and having no bleeding complications or an un-altered or un-disturbed hemostasis.

In certain embodiments, the present invention provides a method of inhibiting pyruvate kinase M2 (PKM2) dimerization by administering a PKM2 inhibitor in a patient in need thereof.

In certain embodiments, the dimerization is inhibited by the PKM2 inhibitor by about 10% to 100% as compared to pre-treatment function. In certain embodiments, the dimerization is inhibited by 10%, 20%, 30%, 40%, 50%, 60%, 70%, 80%, 90% or 100%.

In certain embodiments, the inhibition does not alter hemostasis.

In certain embodiments, the present invention provides a method of treating a disease associated with thrombosis by administering a pyruvate kinase M2 (PKM2) inhibitor in a patient in need thereof. As used herein an "inhibitor of PKM2" inhibits PKM2 dimerization. In certain embodiments, the PKM2 inhibitor is a member of the thieno[3,2-b]pyrrole[3,2-d]pyridazinones class, such as ML265 or TEPP-46 or CID-44246499 or NCGC00186528. In certain embodiments, the PKM2 inhibitor is a member of the thieno[3,2-b]pyrrole[3,2-d]pyridazinones substituted N,N'-diarylsulfonamides, such as a series of N,N0-diarylsulfonamides, 2-Oxo-N-aryl-1,2,3,4-tetrahydroquinoline-6-sulfonamides. In certain embodiments, the PKM2 inhibitor is a member of the 3-(trifluoromethyl)-1H-pyrazole-5-carboxamide class. In certain embodiments, the PKM2 inhibitor is 3-[[4-(2,3-dihydro-1,4-benzodioxin-6-yl)sulfonyl]-1,4-diazepan-1-yl]sulfonyl]aniline (DASA). Matsui et al., Discovery and structure-guided fragment-linking of 4-(2,3-dichlorobenzoyl)-1-methyl-pyrrole-2-carboxamide as a pyruvate kinase M2 activator, *Bioorg & Med. Chem.* 25 (2017) 3540-3546.

In certain embodiments, the PKM2 dimerization inhibitor is an ML265 compound:

5H-Thieno[2',3':4,5]pyrrolo[2,3-d]pyridazin-5-one, 4,6-dihydro-6-[(3-hydroxyphenyl)methyl]-4-methyl-2-(methylthio)-;

5H-Thieno[2',3':4,5]pyrrolo[2,3-d]pyridazin-5-one, 4,6-dihydro-6-[(3-hydroxyphenyl)methyl]-4-methyl-2-(methylsulfinyl)-;

5H-Thieno[2',3':4,5]pyrrolo[2,3-d]pyridazin-5-one, 4,6-dihydro-6-[(3-methoxyphenyl)methyl]-4-methyl-2-(methylsulfinyl)-;

5H-Thieno[2',3':4,5]pyrrolo[2,3-d]pyridazin-5-one, 4,6-dihydro-2,4-dimethyl-6-(phenylmethyl)-;

5H-Thieno[2',3':4,5]pyrrolo[2,3-d]pyridazin-5-one, 4,6-dihydro-6-[(4-methoxyphenyl)methyl]-2,4-dimethyl-;

5H-Thieno[2',3':4,5]pyrrolo[2,3-d]pyridazin-5-one, 6-[(4-fluorophenyl)methyl]-4,6-dihydro-2,4-dimethyl-; or 5H-Thieno[2',3':4,5]pyrrolo[2,3-d]pyridazin-5-one, 6-[(2-fluorophenyl)methyl]-4,6-dihydro-2,4-dimethyl-.

As used herein an "activator/stabilizer of tetramer PKM2" activates or stabilizes tetrameric PKM2. In certain embodiments, activator/stabilizer of tetramer PKM2 is N,N0-diarylsulfonamides; thieno[3,2-b]pyrrole[3,2-d]pyridazinones; 2-oxo-N-aryl-1,2,3,4-tetrahy-droquinoline-6-sulfonamides; quinolone sulfonamides; 1-(sulfonyl)-5-(arylsulfonyl)indoline; 2-((1H-benzo[d]imida-zol-1-yl)methyl)-4H-pyrido[1,2-a]pyrimidin-4-ones; or 3-(trifluoromethyl)-1H-pyrazole-5-carboxamide. In certain embodiments, the activator/stabilizer is 4H-pyrido[1,2-a]pyrimidin-4-one, 2-(1H-benzimidazol-1-ylmethyl)-7-methyl-; 2-(1H-Benzimidazol-1-ylmethyl)-6-methyl-4H-pyrido[1,2-a]pyrimidin-4-one; or 2-(1H-Benzimidazol-1-ylmethyl)-7-methyl-4H-pyrido[1,2-a]pyrimidin-4-one.

In certain embodiments, the platelet function or thrombosis is inhibited by the PKM2 inhibitor by about 10%. In certain embodiments, the thrombosis is inhibited by 10%, 20%, 30%, 40%, 50%, 60%, 70%, 80%, 90% or 100%. In certain embodiments, platelet function and/or thrombosis is inhibited by more than 60-70%.

In certain embodiments, the inhibition does not alter hemostasis.

The terms "treat," "treatment," or "treating" to the extent it relates to a disease or condition includes inhibiting the disease or condition, eliminating the disease or condition, and/or relieving one or more symptoms of the disease or condition. The terms "treat," "treatment," or "treating" also refer to both therapeutic treatment and/or prophylactic treatment or preventative measures, wherein the object is to prevent or slow down (lessen) an undesired physiological change or disorder, such as, for example, the development of thrombosis. For example, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treat," "treatment," or "treating," can also mean prolonging survival as compared to expected survival if not receiving treatment. Those in need of treatment include those already with the disease or disorder as well as those prone to have the disease or disorder or those in which the disease or disorder is to be prevented. In one embodiment "treat," "treatment," or "treating" does not include preventing or prevention.

In certain embodiments, the present invention treats a disease associated with thrombosis by administering a pyruvate kinase M2 (PKM2) inhibitor in a patient in need thereof. In certain embodiments, the disease associated with thrombosis is myocardial infarction, deep vein thrombosis, stroke, diabetes associated thrombosis, cancer associated thrombosis, peripheral arterial disease. In certain embodiments, the disease associated with thrombosis is coronary artery disease.

In certain embodiments, the treating prevents the formation of thrombosis.

In certain embodiments, the administration is by oral administration, intravenous infusion, intraperitoneal administration.

The phrase "therapeutically effective amount" or "effective amount" includes but is not limited to an amount of a compound of the that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "mammal" as used herein refers to humans, higher non-human primates, rodents, domestic, cows, horses, pigs, sheep, dogs and cats. In one embodiment, the mammal is a human. The term "patient" or "subject" as used herein refers to any animal including mammals. In one embodiment, the patient is a mammalian patient. In one embodiment, the patient is a human patient.

Therapeutic Agents

In certain embodiments, the PKM2 inhibitor ML265 or DASA.

As used herein an "inhibitor of PKM2" inhibits PKM2 dimerization. In certain embodiments, the PKM2 inhibitor is a member of the thieno[3,2-b]pyrrole[3,2-d]pyridazinones class, such as ML265 or TEPP-46 or CID-44246499 or NCGC00186528. In certain embodiments, the PKM2 inhibitor is a member of the thieno[3,2-b]pyrrole[3,2-d]pyridazinones substituted N,N'-diarylsulfonamides, such as a series of N,N0-diarylsulfonamides, 2-Oxo-N-aryl-1,2,3,4-tetrahydroquinoline-6-sulfonamides. In certain embodiments, the PKM2 inhibitor is a member of the 3-(trifluoromethyl)-1H-pyrazole-5-carboxamide class. In certain embodiments, the PKM2 inhibitor is 3-[[4-(2,3-dihydro-1,4-benzodioxin-6-ylsulfonyl)-1,4-diazepan-1-yl]sulfonyl]aniline (DASA).

As used herein an "activator/stabilizer of tetramer PKM2" activates or stabilizes tetrameric PKM2. In certain embodiments, activator/stabilizer of tetramer PKM2 is N,N0-diarylsulfonamides; thieno[3,2-b]pyrrole[3,2-d]pyridazinones; 2-oxo-N-aryl-1,2,3,4-tetrahy-droquinoline-6-sulfonamides; quinolone sulfonamides; 1-(sulfonyl)-5-(arylsulfonyl)indoline; 2-((1H-benzo[d]imida-zol-1-yl)methyl)-4H-pyrido[1,2-a]pyrimidin-4-ones; or 3-(trifluoromethyl)-1H-pyrazole-5-carboxamide.

In certain embodiments, the quinolone sulfonamide is 8-Quinolinesulfonamide, N-[4-[[4-(cyclopropylmethyl)-1-piperazinyl]carbonyl]phenyl]-; Benzenesulfonamide, N-[4-[[4-(2-methoxyphenyl)-1-piperazinyl]carbonyl]phenyl]-; Benzenesulfonamide, 3-chloro-N-[4-[(4-phenyl-1-piperazinyl)carbonyl]phenyl]-; 3-chloro-N-[4-[(4-phenyl-1-piperazinyl)carbonyl]phenyl]Benzenesulfonamide; 3-chloro-N-[4-(4-phenylpiperazine-1-carbonyl)phenyl]benzenesulfonamide; or 3-chloro-N-[4-(4-phenylpiperazine-1-carbonyl)phenyl]benzene-1-sulfonamide.

In certain embodiments, the activator/stabilizer of tetramer PKM2 is a tetrahyro quinoline sulfonamide: 6-Quinolinesulfonamide, N-(4-fluorophenyl)-1,2,3,4-tetrahydro-2-oxo-; or 6-Quinolinesulfonamide, N-(2-fluorophenyl)-1,2,3,4-tetrahydro-2-oxo-.

In certain embodiments, the dimeric PKM2 inhibitor is ML265 or DASA.

In certain embodiments, ML265 was first dissolved in DMSO, then mixed with water before administration. Alternatively, 40% W/V Solutol (HS-15) in water can be used. As it has a short half-life, it can be formulated as extended-release tablets or pills to keep the therapeutic dose at a steady level in the body for longer periods of time.

The pharmaceutical compositions of the invention can comprise one or more excipients. When used in combination with the pharmaceutical compositions of the invention the term "excipients" refers generally to an additional ingredient that is combined with the PKM2 inhibitor to provide a corresponding composition. For example, when used in combination with the pharmaceutical compositions of the invention the term "excipients" includes, but is not limited to carriers, binders, disintegrating agents, lubricants, sweetening agents, flavoring agents, coatings, preservatives, and dyes.

The PKM2 inhibitor can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard- or soft-shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices. In certain embodiments, the composition is formulated for extended release.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the PKM2 inhibitor can be determined by comparing their in vitro activity, and in vivo activity in animal models. Methods for the extrapolation of effective dosages in mice, and other animals, to humans are known to the art; for example, see U.S. Pat. No. 4,938,949.

The amount of the PKM2 inhibitor required for use in treatment will vary with the route of administration, and the age and condition of the patient, and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Certain embodiments of the invention will now be illustrated by the following non-limiting Example.

Example 1

Manipulating Metabolic Plasticity in Platelets by Targeting Pyruvate Kinase M2 to Inhibit Thrombosis Recently, metabolic pathways are increasingly recognized as potential targets for therapeutic interventions. Although bioenergetic profile studies performed in platelets suggest the existence of metabolic plasticity, very little is known about the mechanistic role of cellular metabolism in platelet function. Pyruvate kinase (PK) is a key enzyme that catalyzes the final step of glycolysis, which involves an irreversible trans-phosphorylation of phosphoenolpyruvate (PEP) to produce pyruvate and ATP.

Mammalian genomes express four kinds of PK isoforms (PKL, PKR, PKM1, and PKM2). PKL is expressed primarily in liver cells, whereas PKR expression is limited to red blood cells. Most other types of cells express the alternatively spliced products of the PKM gene, either PKM1 and/or PKM2. The PKM1 isoform is expressed in most adult tissues that have high catabolic demands, such as muscle and brain, whereas PKM2 is primarily expressed in highly proliferative cells such as stem cells, embryonic cells, and tumor cells that are characterized by high anabolic demand. Unlike other isoforms of PK that function only as tetramers, PKM2 exists in both tetrameric and dimeric forms. While PKM1 and tetrameric PKM2 favor ATP production from oxidative phosphorylation (OXPHOS) through the tricarboxylic acid (TCA) cycle, dimeric PKM2 is a crucial regulator of aerobic glycolysis (conversion of glucose to lactate in the presence of oxygen, a phenomenon referred to as the "Warburg effect" in tumor cells) and facilitates the production of lactate and metabolic reprogramming. Platelets contain PKM1, but the existence of PKM2 in platelets, and its physiological significance is not well understood. One possibility is that PKM2 may contribute to multiple aspects of platelet function by regulating glycolysis and the TCA cycle. Another possibility is that PKM2 may regulate platelet function by acting as a phosphorylase, an activity that is unique to PKM2 rather than PKM1.

In this study, using comprehensive metabolomic analysis of human platelets, we report that PKM2 regulates the metabolism of glycerophospholipids and arachidonic acid, which are known to contribute to platelet activation. Limiting PKM2 dimer formation by the small molecule ML265 reduced stimulus-dependent platelet function by downregulating PI3 kinase-mediated Akt/GSK3 signaling both in human and murine platelets. Genetic deletion of PKM2 specifically in murine platelets inhibited stimulus-dependent platelet activation and aggregation in vitro and arterial thrombosis in vivo. These findings suggest that manipulating metabolic plasticity by targeting dimeric PKM2 could be a potential future target for anti-thrombotic therapeutic intervention.

Results

PKM2 Regulates Metabolic Plasticity by Modulating Glycolytic, Glycerophospholipid and Fatty Acid Metabolic Pathways in Human Platelets Using immunoblotting, it was first confirmed the presence of PKM2 in human and murine platelets (FIG. 1A). PKM2 exists as tetramer and dimer in most cells. Compared to quiescent platelets, a marked increase in PKM2 dimer was observed in human platelets stimulated with convulxin or thrombin (FIG. 1B). ML265, a small molecule that is known to stabilize tetramerization and limit PKM2 dimerization, decreased PKM2 dimers in the human platelets stimulated with convulxin or thrombin (FIG. 1B). Dimeric PKM2 is known to regulate lactate production via aerobic glycolysis. Therefore, it was next determined whether limiting PKM2 dimer formation reduces lactate production by regulating glycolysis. Compared to resting platelets, a ~two-fold increase in glucose uptake and lactate production was observed in platelets stimulated with convulxin or thrombin, which was significantly decreased in ML265 pre-treated groups (FIGS. 1C & D). Together, these results suggest that dimeric PKM2 promotes lactate production by regulating glycolysis in platelets.

Figure 8:
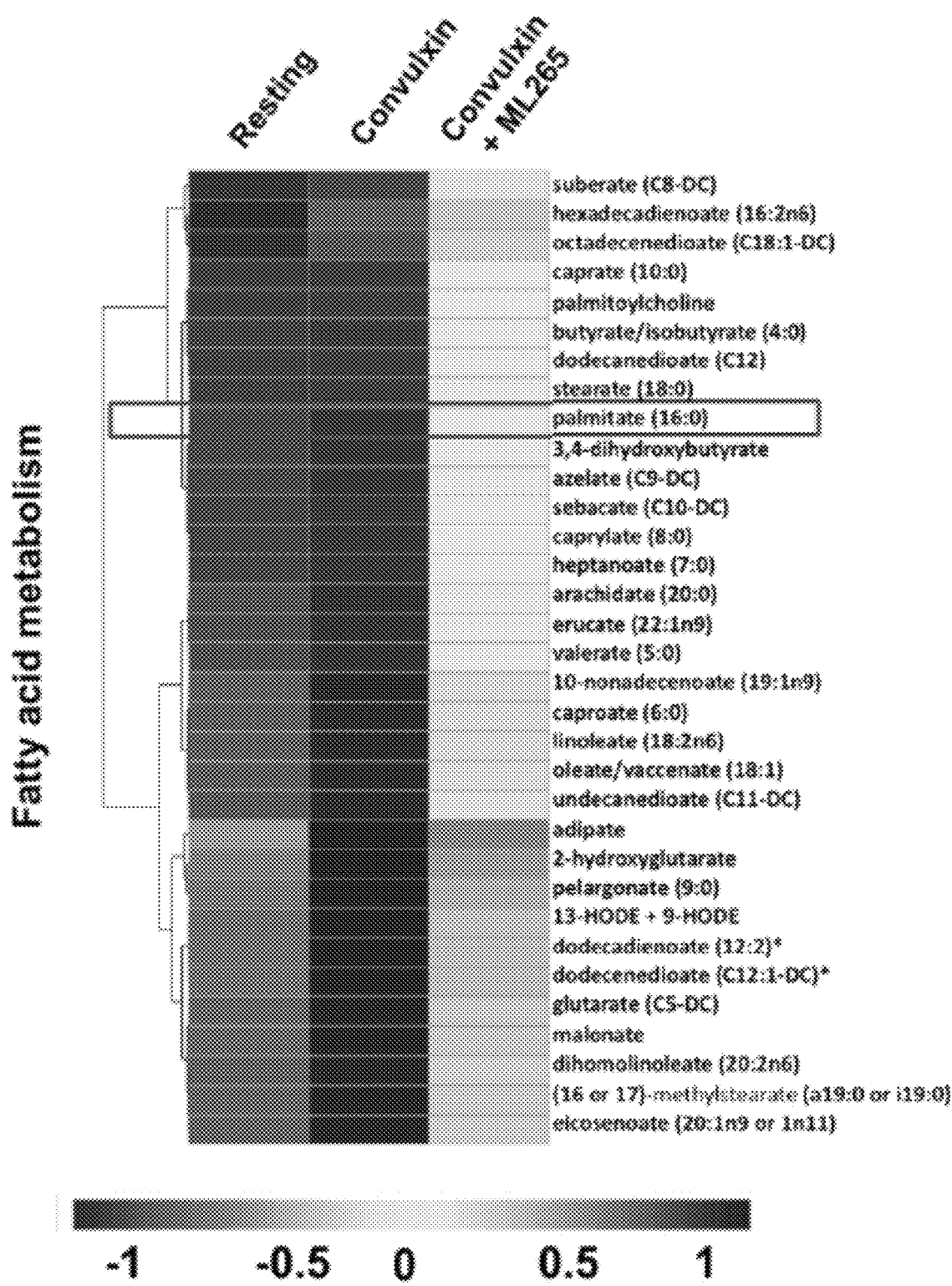
FIG. 8. Metabolite enrichment analysis of fatty acid metabolism. Columns represent individual groups, and rows represent metabolites. Red boxes show palmitate (a main component of β-oxidation), which was downregulated in ML265 pre-treated activated platelets compared to control. n=5 individual donors/group. Welch's two-sample t-test.

To better understand the role of PKM2 dimer in regulating metabolic plasticity in platelets, a comprehensive metabolomic analysis of human platelets was performed. Heatmap analysis suggested a change in the levels of several metabolites in convulxin-stimulated platelets compared to resting platelets, and the metabolic response to convulxin was altered in the ML265 pre-treated group (FIG. 1E). Metabolite enrichment analysis further confirmed that ML265 altered several metabolites in the glycolytic pathway, including glucose uptake and lactate production (FIG. 1E). Interestingly, these results indicated that dimeric PKM2 promotes the synthesis of pro-thrombotic metabolites of glycerophospholipid metabolism, including glycerophospholchoine, choline, and glycerophosphoethanolamine. ML265 also altered levels of arachidonic acid and 12-hydroxyeicosatetraenoic acid (12-HETE), which are endogenous agonists known to potentiate platelet activation (FIG. 1E). As anticipated in convulxin-stimulated platelets, a reduction in platelet arachidonate level was observed, which is due to its utilization for the synthesis of thromboxane A2 ($TxA_2$) and 12-HETE. A further decrease in arachidonate was observed in convulxin-stimulated platelets that were pre-treated with ML265. This might be attributed to the reduction in the synthesis of glycerophospholipid metabolites that lead to the production of arachidonate. In line with these observations, levels of $TxB_2$ (a stable metabolite of $TxA_2$) were reduced in convulxin-stimulated platelets that were pre-treated with ML265 (FIG. 1F). Additionally, it was observed that ML265 altered the level of free fatty acids and palmitate, which are regarded as principal components of fatty acid metabolism and beta-oxidation (FIG. 8). Together, these results suggest that dimeric PKM2 regulates metabolic plasticity, including glycolytic, glycerophospholipid, and fatty acid metabolism, that may contribute to various aspects of platelet activation.

PKM2 Modulates Multiple Aspects of Platelet Activation

Figures 2A, 2B, 2C, 2D, 2E, 2F:
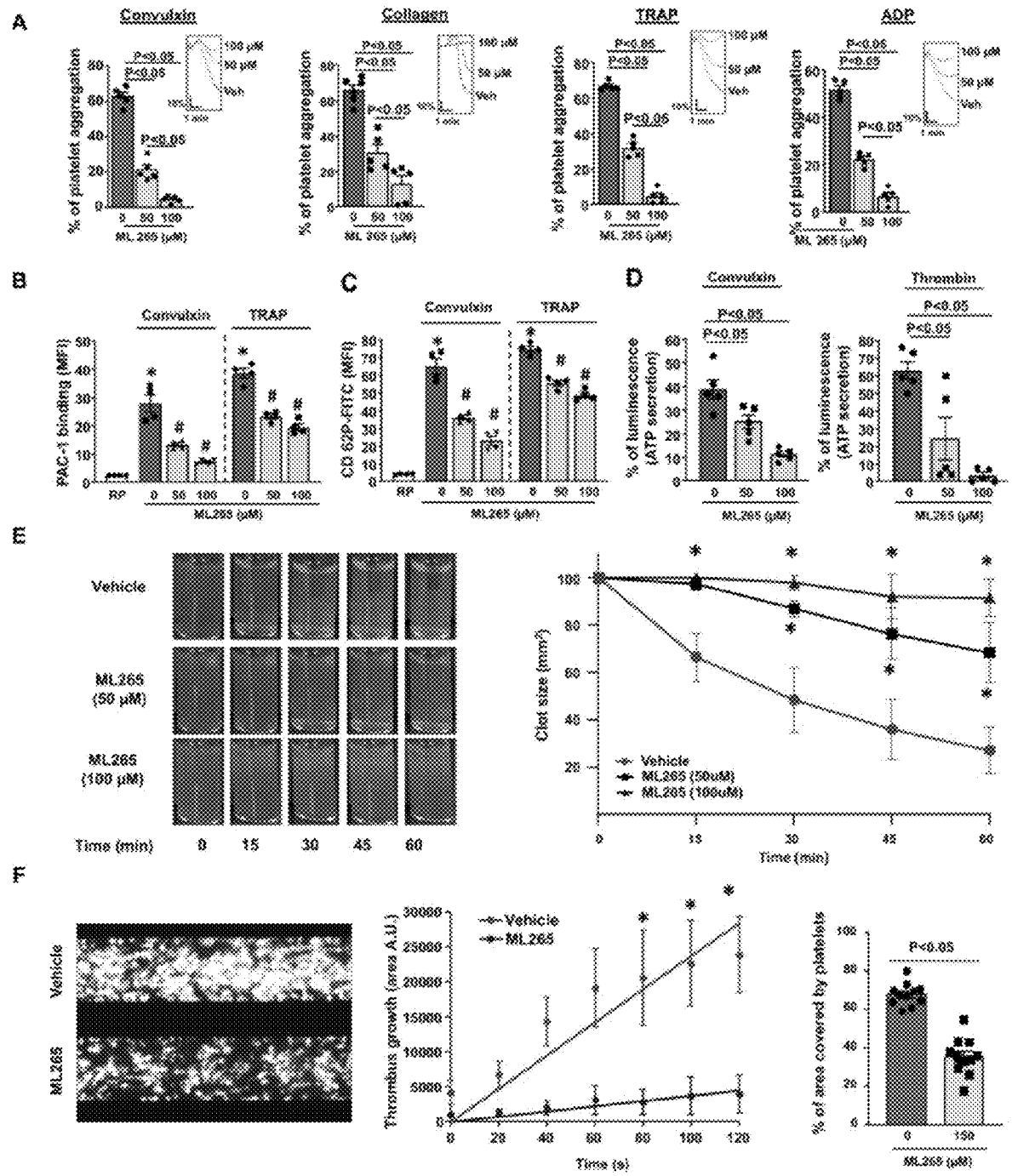
FIGS. 2A-2F.
Figures 9A, 9B:
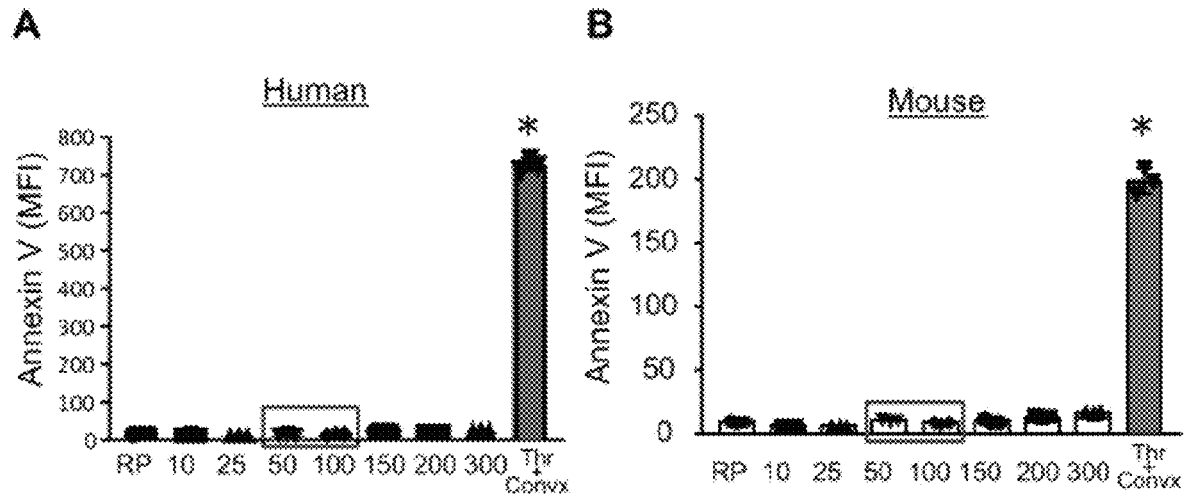
FIGS. 9A-9B. ML265 does not induce apoptosis in resting platelets. Annexin V binding in human (left panel, n=3 individual donors/group) and mouse (right panel, n=3 mice/group) platelets treated with increasing concentrations of ML265. Platelets stimulated with thrombin (0.1 U/ml) and convulxin (100 ng/ml) was used as a positive control. Red boxes denote the concentration of ML265 used in most of the in vitro studies. *P<0.05 vs. resting platelets. One-way ANOVA followed by Tukey's multiple comparisons test.

Next, the effect of dimeric PKM2-mediated metabolic plasticity on platelet function in vitro and ex vivo was determined using a microfluidic chamber system. Compared to control, human platelets pretreated with ML265 exhibited reduced stimulus-dependent platelet aggregation in response to multiple agonists, including GPVI agonists (convulxin and collagen) and GPCR agonists (TRAP and ADP), in a dose-dependent manner (FIG. 2A). Phosphatidylserine expression on the platelet surface (a marker of platelet apoptosis) was evaluated using flow cytometry with annexin V to rule out the possibility that ML265-mediated reduced platelet aggregation may be an outcome of apoptosis. ML265 up to a concentration of 300 µM did not induce phosphatidyl serine surface expression on human platelets (FIGS. 9A-9B). Consistent with the inhibition of platelet aggregation, convulxin or TRAP-induced activation of αIIbβ3 (detected by PAC-1 binding) was decreased in human platelets pretreated with ML265 (FIG. 2B). Furthermore, we observed a significant decrease in α-granule (P-selectin exposure) and dense-granule (ATP release) secretion in stimulus-activated platelets pretreated with ML265 (FIGS. 2C & 2D). Together, these results suggest that dimeric PKM2 regulates integrin αIIbβ3 "inside-out" signaling. Next, integrin αIIbβ3-mediated clot retraction was examined. It was found that clot retraction was significantly inhibited in human platelets pretreated with ML265 in a dose-dependent manner after thrombin stimulation (FIG. 2E), suggesting that dimeric PKM2 also regulates integrin αIIbβ3 "outside-in" signaling. Using a microfluidic flow chamber system, it was next determined whether ML265 is able to inhibit thrombosis ex vivo in the presence of other blood cells. Whole human blood was perfused on collagen (100 µg/ml) coated surface at an arterial shear rate (1500 $s^{-1}$) for 5 minutes in the absence or presence of ML265. The size of thrombi was determined by measuring the surface area coverage of fluorescently labeled platelets. At a dose of 50 or 100 µM, no significant difference was observed in thrombus formation in the ML265 treated group when compared to vehicle control (not shown). However, at a dose of 150 µM, a marked reduction (~5 fold) in the thrombus growth rate and percent of the area covered by platelets was observed in the ML265 treated group when compared with vehicle control (FIG. 2F).

Figures 3A, 3B, 3C, 3D, 3E, 3F:
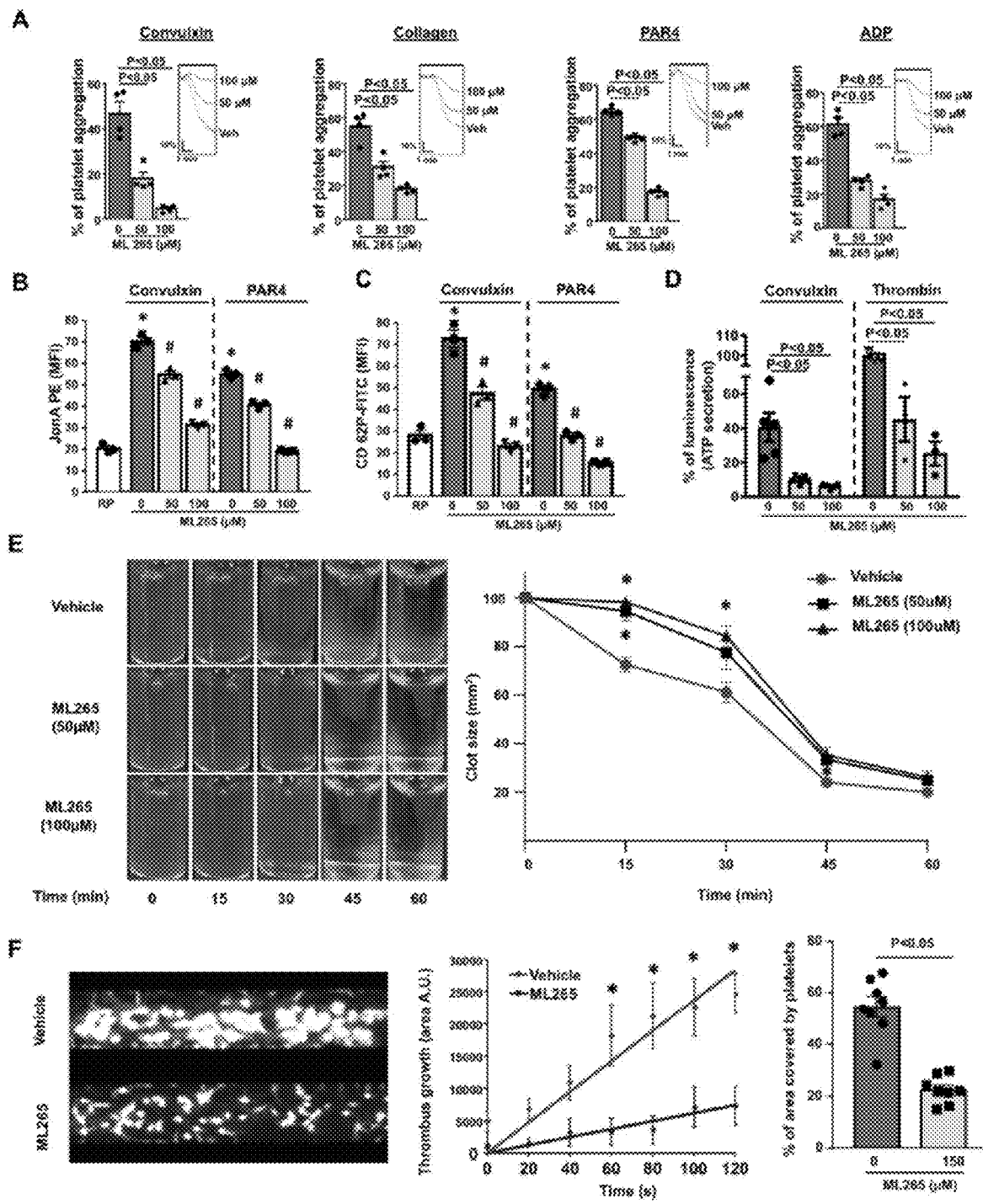
FIGS. 3A-3F. Dimeric PKM2 regulates multiple aspects of platelet function in murine platelets. (A) Mouse platelet-rich plasma pre-treated with vehicle or ML265 and stimulated with agonists including convulxin (50 ng/ml), collagen (1 µg/ml), PAR4 (75 µM) or ADP (5 µM). Results are expressed as the percentage change in light transmission with respect to a blank (platelet-poor plasma/buffer without platelets), set at 100%. The upper panel in each bar graph denotes the representative aggregation curves (blue: control; black: 50 µM ML265; red: 100 µM ML265). Values are mean±SEM, with n=4 mice/group. *P<0.05 vs control. One-way ANOVA followed by Tukey's multiple comparisons test. (B, C and D) Effect of dimeric PKM2 inhibition on integrin αIIbβ3 activation, P-selectin surface expression, and ATP secretion from dense granules in platelets stimulated with convulxin (100 ng/ml), PAR4 (75 µM) or thrombin (0.1 U/ml). Values are mean±SEM, n=3-5 mice/group. *P<0.05 vs. resting platelets, #P<0.05 vs. vehicle. Two-way ANOVA (B & C) and One-way ANOVA (D) followed by Tukey's multiple comparisons. (E) Clot retraction was measured for 1 hr in platelet-rich plasma, supplemented with RBC, after adding 0.25 U/ml thrombin in the presence of a vehicle or ML265 (50 and 100 µM). The left panels show representative images at different time points. The right panel shows the quantification of clot size with time. PRP was pooled from 5 mice in each group. Values are mean±SEM, n=3 experiments/group. Two-way ANOVA with Tukey's multiple comparison test. (F) Mouse whole blood pretreated with vehicle or ML265 (150 µM) was perfused over a collagen-coated (100 µg/mL) surface for 5 minutes at a shear rate of $1500\ s_{-1}$ in a flow chamber system from Bioflux Microfluidics. The left panel shows the representative image at the end of the assay. The middle panel shows the thrombus growth on collagen matrix over time. Slopes over time showed that the rate of thrombus growth in ML265 treated whole blood (slope: 61.65) was decreased when compared with vehicle control (slope: 236.1). Values are mean±SEM, with n=3 mice/group. * indicates P<0.05. Two-way ANOVA with Tukey's multiple comparison test. The right panel shows the surface area covered by fluorescent platelets after 5 minutes of perfusion. 3 to 4 areas from different areas of the flow chamber were analyzed from each blood sample, Values are mean±SEM, with n=8 areas/group. Mann-Whitney test.
Figures 10A, 10B:
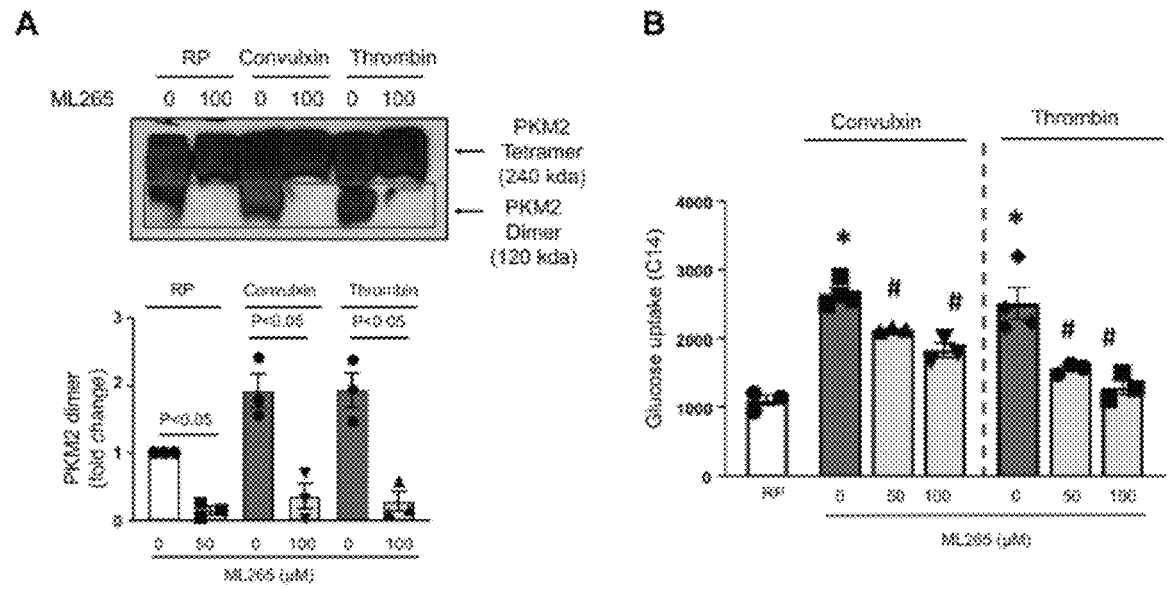
FIGS. 10A-10B. PKM2 inhibits dimerization and inhibits glucose uptake in activated mouse platelets. (A) The top panel shows representative Western blot, non-reducing (native), of PKM2 dimer and tetramer expression in platelets pre-treated with vehicle or ML265 and stimulated with agonists including convulxin (100 ng/ml) or thrombin (0.1 U/mL). Red box denote the PKM2 dimers. The lower panel shows the densitometry analysis of immunoblots. Values are mean±SEM, n=3 mice/group. Two-way ANOVA followed by Tukey's multiple comparisons test. (B) Effect of PKM2 inhibition on glucose uptake in stimulated-platelets with convulxin (100 ng/ml) and thrombin (0.1 U/ml). Values are mean±SEM, n=3 mice/group. *P<0.05 vs. resting platelets; #P<0.05 vs. activated platelets (vehicle). Two-way ANOVA followed by Tukey's multiple comparisons test.

To determine whether dimeric PKM2 also regulates platelet function in mice, the inhibitory effects of ML265 on multiple aspects of platelet function was examined using murine platelets. First, it was confirmed that ML265 limits PKM2 dimer formation by stabilizing tetramers and reduces glucose uptake in platelets stimulated with agonists. It was observed that, similar to its effects in human platelets, ML265 limited PKM2 dimer formation and reduced glucose uptake in platelets stimulated with convulxin or thrombin (FIGS. 10A-10B). ML265-pretreated platelets exhibited reduced stimulus-dependent platelet aggregation with multiple agonists, including GPVI agonists (convulxin and collagen) and GPCR agonists (PAR4 and ADP), when compared to vehicle control (FIG. 3A). Consistent with the inhibition of platelet aggregation, convulxin and PAR4-induced activation of αIIbβ3 (detected by JONA binding) was decreased in ML265 pretreated mouse platelets (FIG. 3B). Furthermore, a significant decrease in α-granule secretion (P-selectin exposure), dense-granule secretion (ATP release), and clot retraction in stimulus-activated ML265-pretreated platelets was observed (FIGS. 3C, 3D, and 3E). It was next determined whether ML265 is able to inhibit thrombus formation in vitro, in the presence of other blood cells using a microfluidic flow chamber system. Similar to humans, a marked reduction in thrombus growth rate and percent of the area covered by platelets was observed in the ML265 treated group when compared with vehicle control (FIG. 3F). Together, these results suggest that PKM2 modulates multiple aspects of platelet function in both human and murine platelets.

Figures 4A, 4B, 4C, 4D, 4E, 4F:
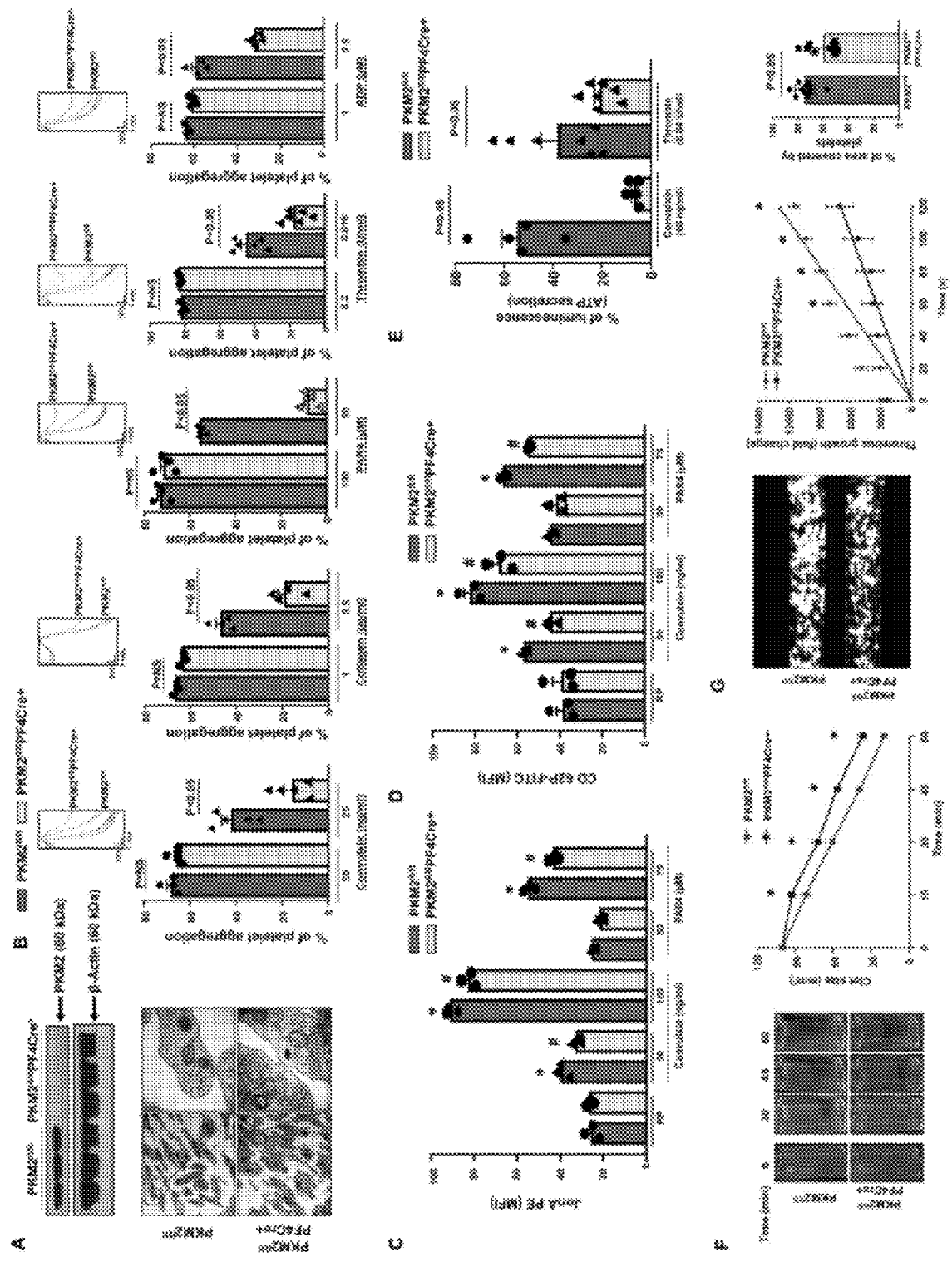
FIGS. 4A-4F. Platelet/megakaryocyte-specific PKM2-deficient mice exhibits decreased platelet function in standardized in vitro assays. (A) The upper panel shows the Western blot of PKM2 (upper panel) in platelets from $PKM2_{fl/fl}$ and $PKM2_{fl/fl}PF4Cre+$ mice. The individual lanes are from 3 different mouse/group. The lower panel shows transmission emission micrography of platelets. The inset in the boxed region is magnified and shown in microphotograph. Scale bar: 0.5 (B) Platelet-rich plasma or washed platelets from $PKM2_{fl/fl}$ and $PKM2_{fl/fl}PF4Cre+$ were stimulated with different agonists, including convulxin, collagen, PAR4, thrombin, and ADP. Results are expressed as the percentage change in light transmission with respect to the blank (platelet-poor plasma/buffer without platelets), set at 100%. The upper panel in each bar graph denotes the representative aggregation curves (blue and red: $PKM2_{fl/fl}$; black and green: $PKM2_{fl/fl}PF4Cre+$. Values are mean±SEM, n=3-6 mice/group. *P<0.05 vs control. One-way ANOVA followed by Tukey's multiple comparisons test. (C, D and E) Effect of lack of PKM2 on integrin αIIbβ3 activation, P-selectin exposure, and ATP secretion from dense granules in stimulated-platelets with agonists including convulxin, PAR4, and thrombin. Values are mean±SEM, n=3-7 mice/group. *P<0.05 vs. resting platelets, #P<0.05 vs. $PKM2_{fl/fl}$. Two-way ANOVA (C & D) and One-way ANOVA (E) followed by Tukey's multiple comparisons. (F) Clot retraction was measured for one hour in platelet-rich plasma, supplemented with RBC, after adding 0.25 U/ml thrombin. The left panels show the representative images at different time points, and the right panel shows the quantification of the clot size. PRP was pooled from 5 mice in each group. Values are mean±SEM, with n=3 experiments/group. *P<0.05 vs $PKM2_{fl/fl}$. Two-way ANOVA with holm-sidak's multiple comparisons test. (G) Mouse whole blood from $PKM2_{fl/fl}$ or $PKM2_{fl/fl}PF4Cre+$ was perfused over a collagen coated (100 µg/mL) surface for 5 minutes at a shear rate of $1500\ s_{-1}$ in a flow chamber system from Bioflux Microfluidics. The left panel shows the representative image at the end of the assay. The middle panel shows the thrombus growth on collagen matrix over time. Slopes over time showed that the rate of thrombus growth in the $PKM2_{fl/fl}PF4Cre+$ mice (slope: 58.40) was decreased when compared with $PKM2_{fl/fl}$ mice (slope: 108.7). Values are mean±SEM, with n=3 mice/group. * indicates P<0.05. Two-way ANOVA with tukey's multiple comparison test. The right panel shows the surface area covered by fluorescent platelets after 5 minutes of perfusion. 3 to 4 areas from different areas of the flow chamber were analyzed from each blood sample, n=11 areas/group. Mann-Whitney test.
Figure 13:
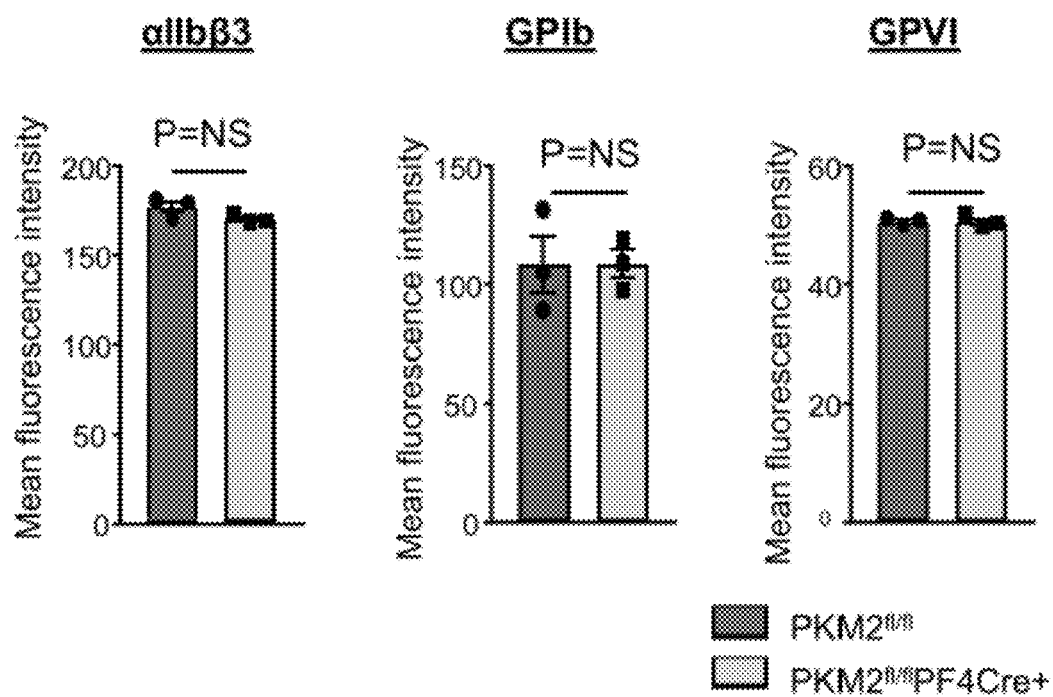
FIG. 13. Expression of platelet adhesion receptors. The expression levels of αIIbβ3, GPIb, and GPVI were analyzed in platelets from PKM2$_{fl/fl}$ or PKM2$_{fl/fl}$PF4Cre+ using flow cytometry. The results are expressed as mean fluorescence intensity (MFI). Values are expressed as mean±SEM, n=3 mice/group. Mann-Whitney test.
Figure 14:
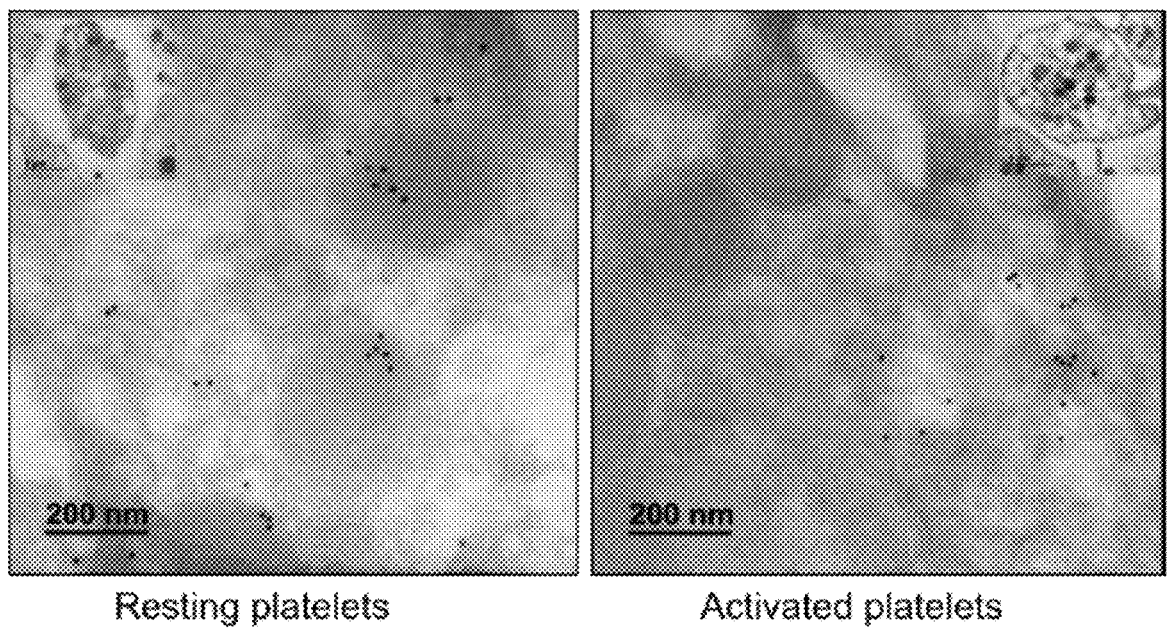
FIG. 14. Immunogold staining of PKM2 in platelets. PKM2 was predominantly localized in the α-granules in resting platelets, whereas in the cytoplasm of activated platelets as determined by immunogold staining using transmission electron microscopy.
Figure 15:
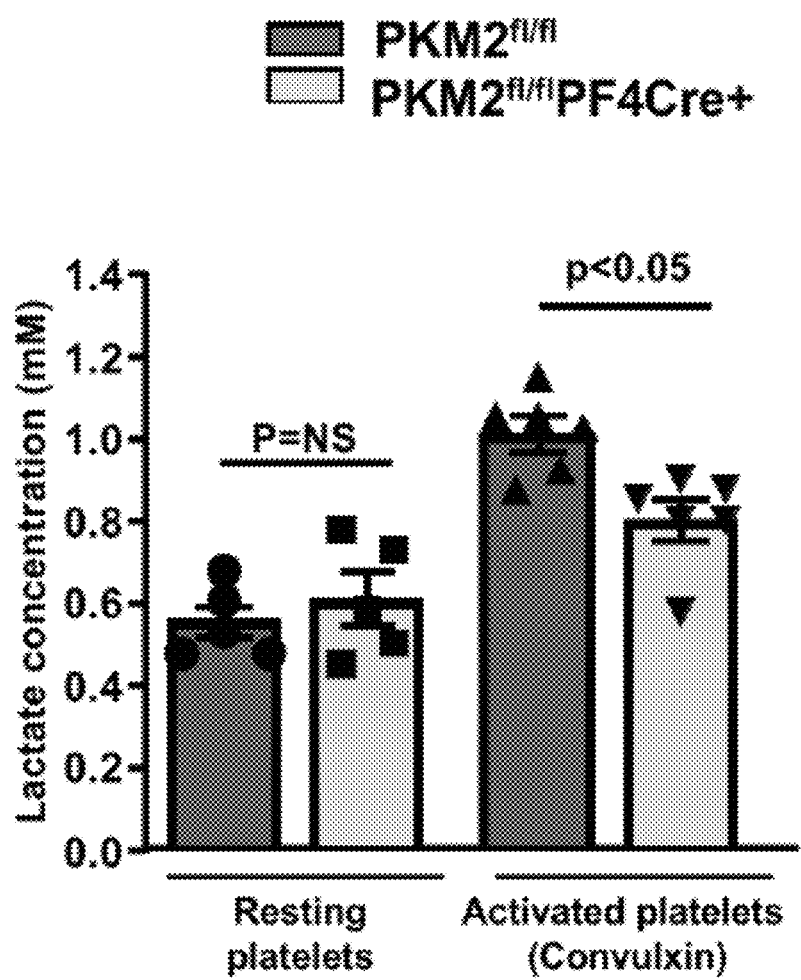
FIG. 15. Lack of PKM2 in murine platelets reduces lactate production. Effect of lack of PKM2 on lactate production in mice platelets stimulated with convulxin (200 ng/ml) Values are mean±SEM, n=5-6 mice/group. One-way ANOVA with Tukey's multiple comparisons test.
Figures 16A, 16B, 16C, 16D:
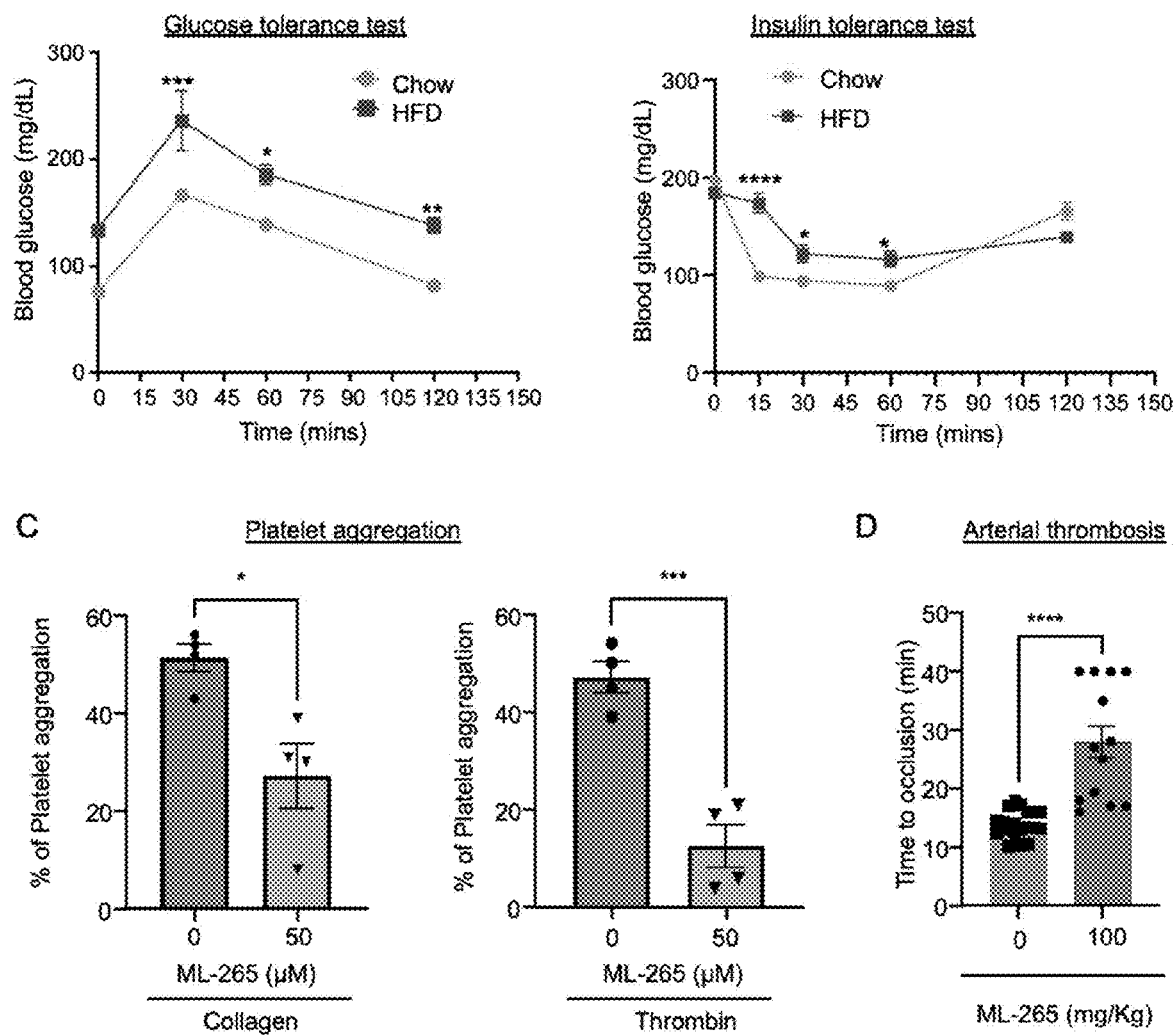
FIGS. 16A-16D. ML265 inhibits platelet aggregation and arterial thrombosis in pre-existing comorbid condition of obesity. Wild-type (C57BL6/J) mice fed a chow and high-fat diet (Cat #TD.06414, Envigo, 60% Kcal from fat) for 4 months. (A) Blood glucose levels (B) Blood glucose levels during the insulin tolerance test. Statistics (A & B): Two-way ANOVA with Tukey's multiple comparisons test (*P<0.05, P<0.01, *P<0.001, ****P<0.0001; n=10 mice/group). (C) Platelet rich plasma or washed platelets from obese mice were pretreated with vehicle or ML265 and stimulated with agonists including collagen (1 μg/mL) and thrombin (0.02 U/mL). The results are represented as percent change light transmission after subtracting the blank (platelet poor plasma/Tyrode's buffer). Statistics: Student t-test (*P<0.05, *P<0.001; n=4 mice/group). (D) 5.0% FeCl$_3$-injury induced carotid artery thrombosis in male obese mice (fed a high-fat diet for 4 months), infused with vehicle or ML265. Statistics: Mann-Whitney U test (**P<0.0001, n=13-18 carotid arteries from 8 to 9 mice/group). All the values are represented as mean±SEM.

Platelet-Specific Deletion of PKM2 Impairs Platelet Activation and In Vitro Thrombus Formation To confirm a mechanistic role for PKM2 in regulating multiple aspects of platelet function and arterial thrombosis, mice were generated that are devoid of PKM2 in megakaryocyte/platelets ($PKM2^{fl/fl}PF4Cre+$) (FIGS. 11A-11B). Western blotting confirmed the lack of PKM2 in platelets (FIG. 4A) but not in peritoneal macrophages of $PKM2^{fl/fl}$ PF4Cre+ mice, suggesting specific deletion of PKM2 from platelets (FIG. 12). The size and morphology of platelets were comparable between $PKM2^{fl/fl}PF4Cre+$ and littermate control $PKM2^{fl/fl}$ mice, as determined by transmission electron microscopy (FIG. 4A). The body weight, complete blood count (Table S1), and expression levels of platelet surface receptors, including integrin αIIbβ3, GPIb, and GPVI were comparable between $PKM2^{fl/fl}PF4Cre+$ and littermate control $PKM2^{fl/fl}$ mice (FIG. 13). Next, the subcellular localization of PKM2 was determined in resting and activated platelets by immunogold staining using transmission electron microscopy. PKM2 was predominantly localized in the α-granules in resting platelets and in the cytoplasm of activated platelets (FIG. 14). Next, the effect of lack of PKM2 on lactate levels was determined. Consistent with the ML265 data in human and murine platelets, lack of PKM2 in platelets resulted in reduced lactate production only in activated platelets but not resting platelets (FIG. 15), suggesting that platelet-specific PKM2 deficient mice could be used as an animal model to further assess the role of PKM2 in regulating multiple aspects of platelet function.

TABLE 1

Body weight and complete blood counts from 8-10 weeks old mice were obtained using an automated veterinary hematology analyzer (ADVIA-120).

|  | PKM2$^{fl/fl}$ | PKM2$^{fl/fl}$PF4Cre+ | P value |
| --- | --- | --- | --- |
| Body weight | 25.49 ± 0.46 | 26.14 ± 0.54 | 0.2739 |
| WBC (10³/μl) | 9.31 ± 1 38 | 8.94 ± 0.93 | 0.6617 |
| RBC (10³/μl) | 10.01 ± 0.23 | 10.01 ± 0.26 | 0.9382 |
| HGB (g/dl) | 12.29 ± 0.47 | 12.11 ± 0.51 | 0.9808 |
| HTC (%) | 50.43 ± 1.08 | 50.00 ± 1.24 | 0.9999 |
| Platelets (10³/μl) | 1339 ± 107.6 | 1218 ± 54.44 | 0.4510 |
| Neutrophils (10³/μl) | 0.23 ± 0.03 | 0.18 ± 0.01 | 0.1667 |
| Monocytes (10³/μl) | 0.07 ± 0.01 | 0.11 ± 0.04 | 0.8042 |

Values are expressed as mean ± SEM.
N = 7-9 mice/group.
P = Non-significant versus control PKM2fl/fl mice.

Next, it was evaluated whether the deletion of PKM2 inhibits integrin αIIbβ3 "inside-out" and "outside-in" signaling similar to ML265. Platelets from PKM2$^{fl/fl}$PF4Cre+ mice exhibited impaired platelet aggregation upon stimulation with convulxin, collagen, PAR4, thrombin, and ADP (FIG. 4B). Consistent with these results, convulxin and PAR4-induced activation of αIIbβ3 (detected by JONA binding) were decreased in PKM2$^{fl/fl}$PF4Cre+ platelets compared to littermate control PKM2$^{fl/fl}$ platelets (FIG. 4C). Furthermore, a significant decrease in α-granule secretion (P-selectin exposure) and dense-granule secretion (ATP release) was found in PKM2$^{fl/fl}$PF4Cre+ platelets compared to littermate control PKM2$^{fl/fl}$ platelets (FIGS. 4D and 4E). Integrin αIIbβ3-mediated clot retraction was also reduced in PKM2$^{fl/fl}$PF4Cre+ platelets compared to control PKM2$^{fl/fl}$ platelets (FIG. 4G). On the collagen-coated microfluidic chamber, the thrombus rate and the percent of the area covered by platelets was significantly decreased in whole blood from PKM2$^{fl/fl}$PF4Cre+ mice when compared to control PKM2$^{fl/fl}$ mice (FIG. 4H). Collectively, these results provide conclusive evidence that PKM2 contributes to platelet activation by regulating diverse aspects of platelet function.

Figures 5A, 5B, 5C, 5D, 5E, 5F:
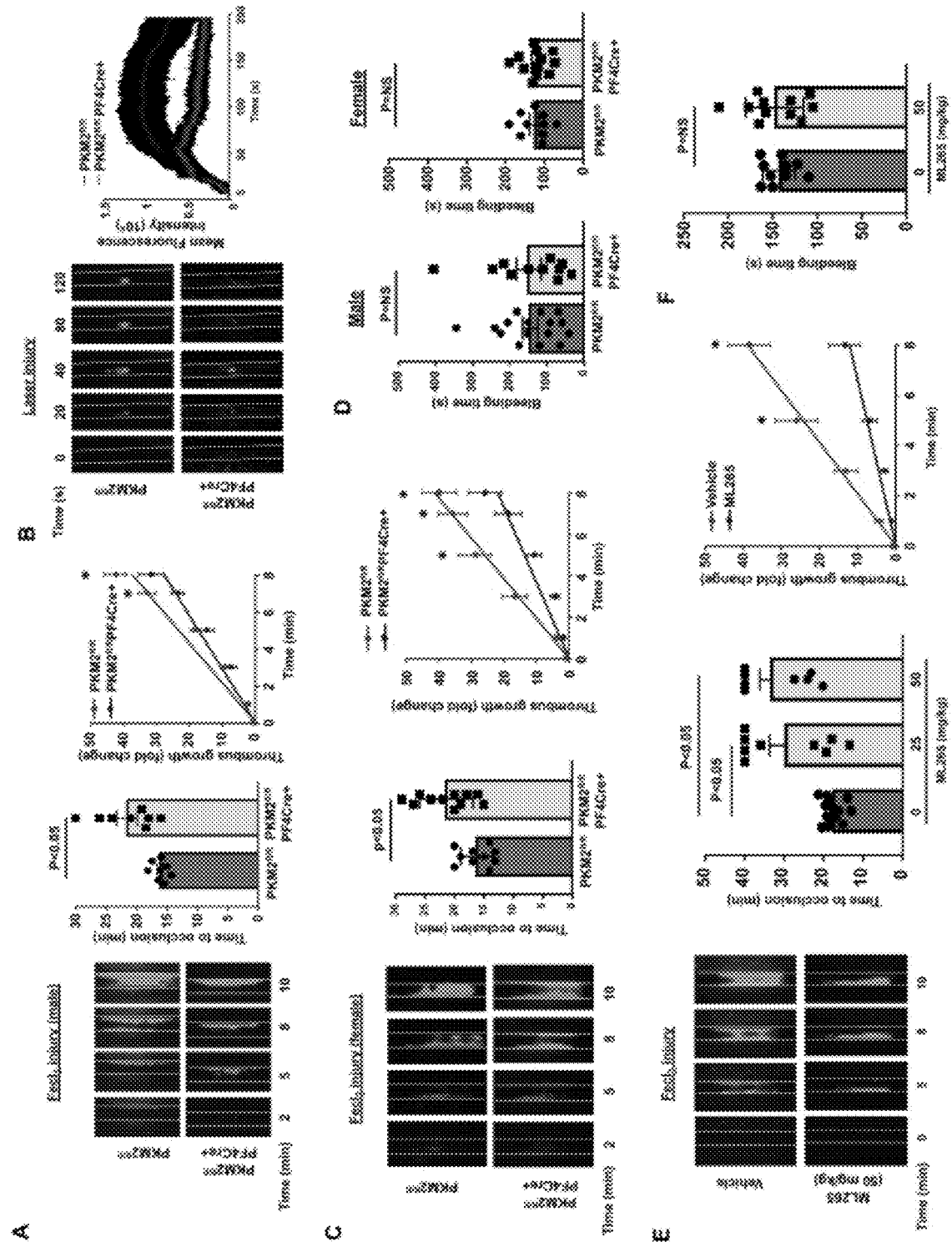
FIGS. 5A-5F. (A) The left panel shows representative microphotographs of carotid artery thrombus (5% FeCl₃ injury) as visualized by upright intravital microscopy in male mice. Platelets were labeled ex vivo with calcein green. White lines delineate the arteries. The middle panel shows time to occlusion (n=8 mice/group). Mann-Whitney test. The right panel shows the rate of thrombus growth (n=8 mice/group). The rate of thrombus growth over a period of two minutes was calculated by dividing the area of the thrombus at time (n) by the area of the same thrombus at time (0) (defined as the time point at which the thrombus diameter first reached 30 µm). Slopes over time showed that the rate of thrombus growth in the PKM2PF4Cre+ mice (slope: 3.488) was decreased when compared with PKM2$_{fl/fl}$ mice (slope: 4.692). * indicates P<0.05. Two-way ANOVA with tukey's multiple comparison test. (B) The left panel shows representative microphotographs of mesenteric artery thrombus (laser injury model) as visualized by upright intravital microscopy in male mice. The right panel shows mean fluorescence intensity (MFI) over time (n=10-12 vessels from 4 mice/genotype). *P<0.05 compared with vehicle control. Mann-Whitney test. (C) The left panel shows representative microphotographs of carotid artery thrombus (5% FeCl₃ injury) as visualized by upright intravital microscopy in female mice. The middle panel shows time to occlusion (n=10-11 mice/group). The right panel shows the rate of thrombus growth (n=8 mice/group). Slopes over time showed that the rate of thrombus growth in the PKM2$_{fl/fl}$PF4Cre+ mice (slope: 2.723) was decreased when compared with PKM2$_{fl/fl}$ mice (slope: 5.175). *indicates P<0.05. Two-way ANOVA with tukey's multiple comparison test. (D) Tail bleeding assay in male and female mice. The tail-transection bleeding time was determined as the time taken for the initial cessation of bleeding after transection. Each symbol represents a single mouse. n=10-16 mice/per group. Mann-Whitney test. (E) The left panel shows representative microphotographs of carotid artery thrombus (5% FeCl3 injury) as visualized by upright intravital microscopy in male mice infused with vehicle or ML265. The middle panel shows time to occlusion. The right panel shows the rate of thrombus growth. Slopes over time showed that the rate of thrombus growth in the ML265 pretreated mice (slope: 1.531) was decreased when compared with vehicle control (slope: 4.862). Values are expressed as ±SEM, n=8-11 mice/group. * indicates P<0.05. Two-way ANOVA with tukey's multiple comparison test. (F) Tail bleeding assay in male mice pretreated with vehicle or ML265. The horizontal bar shows the mean of each group±SEM, n=10-11 per group. Mann-Whitney test.

Targeting PKM2 inhibits arterial thrombosis without altering hemostasis in vivo the role of PKM2 in thrombosis and hemostasis in vivo was evaluated. Approximately eight-week-old male PKM2$^{fl/fl}$ and PKM2$^{fl/fl}$PF4Cre+ mice were subjected to FeCl$_3$ injury-induced carotid artery thrombosis. PKM2$^{fl/fl}$PF4Cre+ mice exhibited smaller thrombi and prolonged time to complete occlusion in injured vessels compared to PKM2$^{fl/fl}$ mice (FIG. 5A). The prolonged time to occlusion in the PKM2$^{fl/fl}$PF4Cre+ mice was concomitant with a decrease in the rate of thrombus growth (FIG. 5A). Susceptibility to arterial thrombosis was evaluated in a second model of thrombosis, laser injury-induced mesenteric artery thrombosis, to ensure that the observed effects are applicable in a broader context. The mean fluorescence intensity of the thrombus was significantly decreased in PKM2$^{fl/fl}$PF4Cre+ male mice compared to PKM2$^{fl/fl}$ mice (FIG. 5B). Irrespective of the model, these results suggest that PKM2 modulates arterial thrombosis in vivo. Next, six to eight-week-old female PKM2$^{fl/fl}$ and PKM2$^{fl/fl}$PF4Cre+ mice were subjected to FeCl$_3$ injury-induced carotid artery thrombosis to assess for sex-based differences. Compared to PKM2$^{fl/fl}$ female mice, PKM2$^{fl/fl}$PF4Cre+ female mice exhibited smaller thrombi and prolonged time to occlusion, concomitant with decreased thrombus growth rate (FIG. 5C). Despite being less susceptible to arterial thrombosis, the tail bleeding time was comparable between PKM2$^{fl/fl}$ and PKM2$^{fl/fl}$PF4Cre+ mice in both males and females, suggesting that lack of PKM2 in platelets does not alter hemostasis (FIG. 5D).

After confirming the role of PKM2 in modulating thrombosis in vivo, the inventors sought to determine the inhibitory effects of ML265 on thrombosis in mice. Eight to ten-week-old male wild-type mice on C57B16/J background with or without ML265 pre-treatment were subjected to FeCl$_3$ induced-carotid artery thrombosis. There was a marked (~4-fold) reduction in the extent of thrombus growth in ML265-treated mice compared to the vehicle-treated group (FIG. 5E). In line with this observation, the time to complete vessel occlusion was significantly prolonged in the mice pretreated with ML265 compared to the vehicle-treated mice. A large number of mice that were pre-treated with ML265 did not occlude after 40 minutes, whereas the time to occlusion for all mice in the control group was approximately 20 mins (FIG. 5E). Based on the anti-thrombotic effects of ML265, its impact on hemostasis was evaluated by measuring the tail-transection bleeding time. The mean time to cessation of bleeding was found to be comparable between the ML265 and vehicle-treated groups, suggesting that ML265 treatment does not alter hemostasis (FIG. 5F). Together, these results suggest that PKM2 regulates arterial thrombosis in vivo, and targeting dimeric-PKM2 with ML265 or similar agents could be used as a potential antithrombotic therapeutic intervention.

PKM2 Regulates PI3K-Mediated Akt/GSK3 Signaling in Platelets

Figures 6A, 6B, 6C:
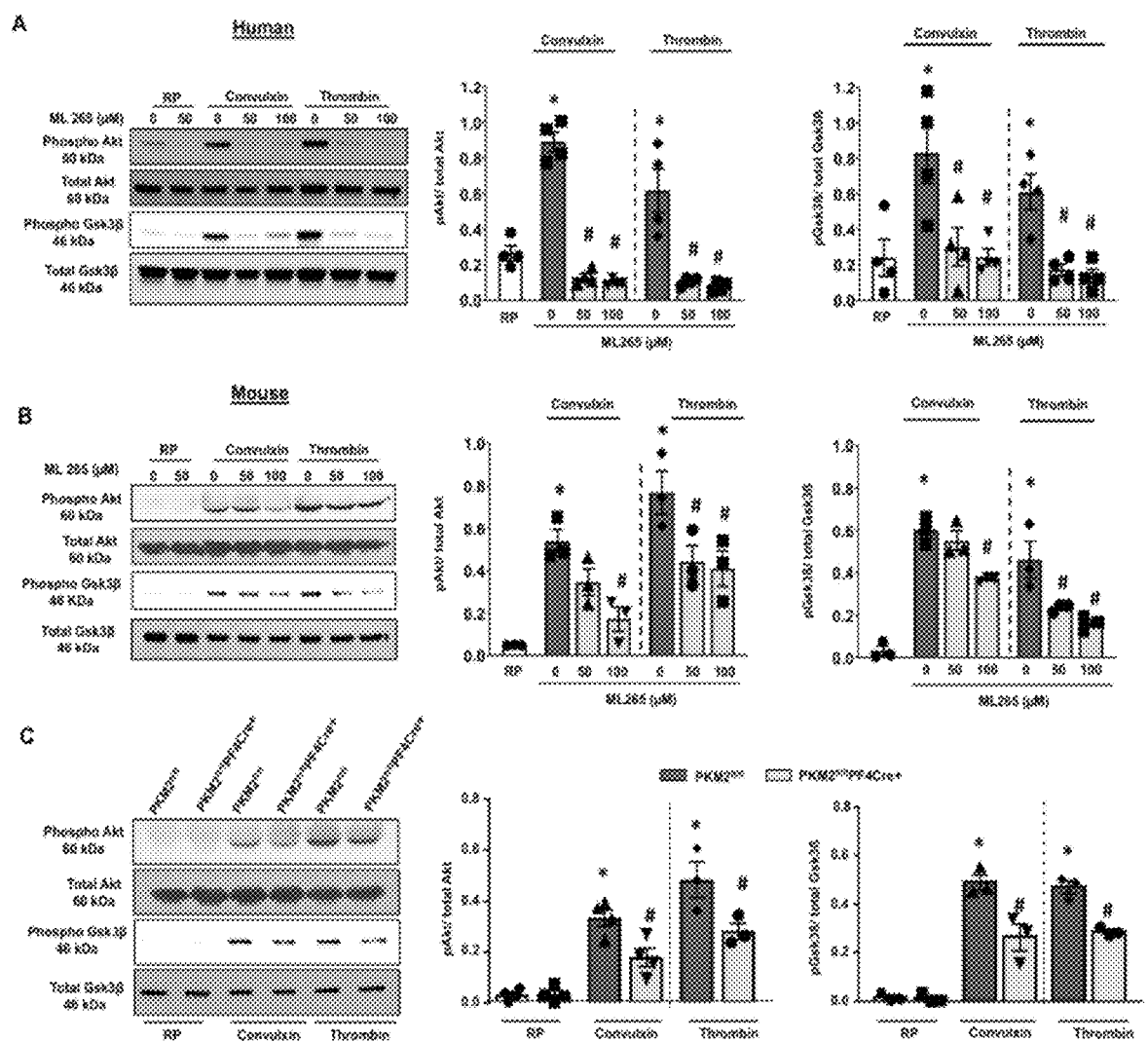
FIGS. 6A-6C. PKM2 regulates PI3 kinase-mediated Akt/GSK3β signaling in platelets. (A and B) Human and mouse platelets were pretreated with vehicle or ML265 (50 and 100 µM) for 10 minutes at room temperature before stimulation with agonists, including convulxin (100 ng/mL) or thrombin (0.1 U/ml) for 10 minutes. The left panels show representative Western blots for phospho-Akt (Ser 473), total Akt, phospho-GSK3β, and total GSK3β. The middle and right panels show densitometry analysis of immunoblots. Values are mean±SEM, n=3-4/group. *P<0.05 vs. resting platelets; #P<0.05 vs. activated platelets (vehicle). Two-way ANOVA with Tukey's multiple comparison test. (C) Platelets from PKM2$_{fl/fl}$ or PKM2$_{fl/fl}$PF4Cre+, were stimulated with convulxin (100 ng/mL) or thrombin (0.1 U/ml) for 10 minutes. The left panels show representative Western blots for phospho-Akt (Ser 473), total Akt, phospho-GSK3β, and total GSK3β. The middle and right panels show densitometry analysis of immunoblots. Values are mean±SEM, n=3-4/group. *P<0.05 vs. resting platelets; #P<0.05 vs. PKM2$_{fl/fl}$. Two-way ANOVA with tukey's multiple comparison test.

Glycerophospholipid metabolism contributes to PI3K-Akt mediated cellular signaling and platelet activation. Because pre-treatment of human platelets with ML265 downregulated glycerophospholipid metabolism and inhibited both "inside-out" and "outside-in" signaling in stimulated platelets, we further determined whether targeting PKM2 with ML265 attenuates PI3K-mediated signaling in human and murine platelets. Pre-treating human platelets with ML265 down-regulated convulxin- or thrombin-mediated Akt and GSK3β phosphorylation compared to vehicle control (FIG. 6A). In line with these observations, pre-treating murine platelets with ML265 also attenuated convulxin or thrombin mediated Akt and GSK3β phosphorylation when compared to vehicle control (FIG. 6B). Consistent with inhibitor studies, genetic deletion of PKM2 in murine platelets reduced stimuli-induced phosphorylation levels of both Akt and GSK3β in response to convulxin or thrombin (FIG. 6C). PKM2 has a phosphorylase activity and may phosphorylate Akt and Gsk3β directly to potentiate platelet activation. However, co-immunoprecipitation studies suggested that PKM2 does not interact with Akt or Gsk3β (not shown), arguing against the possibility that PKM2 phosphorylates Akt and Gsk3β directly. Collectively, these results provide evidence that PKM2 directly or indirectly regulates PI3K-mediated Akt-GSK3β signaling resulting in decreased platelet activation.

Discussion

The interplay between metabolic pathways and cell signaling contributes to several critical processes, including innate and adaptive immunity, carcinogenesis, stem cell proliferation and inflammation. Very little is known about the role of metabolic regulatory mechanisms in platelet activation and thrombosis. Herein, it was found that the glycolytic enzyme PKM2 regulates metabolic plasticity by modulating glycerophospholipid, arachidonic acid, and fatty acid metabolic pathways in human platelets. It was also found that PKM2 mechanistically regulates PI3K-mediated Akt/GSK3 signaling in platelets. Animal studies using platelet-specific PKM2-deficient mice confirmed a role for PKM2 in regulating multiple aspects of platelet function and arterial thrombosis.

Platelet activation is accompanied by an increase in glucose uptake and lactate production. Herein, it was found that stimulus-dependent platelet activation induces dimeric PKM2 expression with increased glucose uptake and lactate production, which could be inhibited using the small molecule ML265. Why is there upregulation of dimeric PKM2 (a driver of aerobic glycolysis) following platelet activation? One possibility is that it may be an adaptive response to fulfill the high energy demand of activated platelets to rapidly form thrombi. Paradoxically, despite less efficiency, the rate of ATP production is 100 times faster in aerobic glycolysis compared to oxidative phosphorylation. Another possibility is to meet other non-energetic cellular metabolic needs to potentiate platelet activation. Interestingly, pathway enrichment analysis revealed that, in addition to the modulation of glycolytic metabolites, dimeric PKM2 regulates levels of pro-thrombotic intermediates of the glycerophospholipid pathway, including glycerophosphochoine, choline and glycerophosphoethanolamine. Glycerophospholipids are known to participate in the synthesis of arachidonic acid, which is a precursor of endogenous platelet agonists for $TxA_2$ and 12-HETE generation. It was found that limiting dimeric PKM2 may regulate $TxA_2$ generation via the glycerophospholipid pathway. Furthermore, we found that dimeric PKM2 regulates levels of free fatty acids and palmitate which suggests that metabolic re-programming of fatty-acid metabolism and beta-oxidation may contribute to the high energy demand of activated platelets.

The present studies also suggest a link between dimeric PKM2-mediated metabolic plasticity and platelet function. It was found that dimeric PKM2 modulates multiple aspects of platelet function in both human and murine platelets in vitro, including integrin αIIbβ3 signaling, alpha and dense-granules secretion, and clot retraction in response to stimulation of GPVI (convulxin and collagen) or GPCR (TRAP and ADP). Furthermore, using whole blood, it was found that dimeric PKM2 regulates platelet aggregation/thrombus formation on a collagen matrix under arterial shear stress conditions in vitro. Together, these results suggest that the presence of the dimeric PKM2 isoform in platelets may provide metabolic plasticity to adapt quickly to cellular responses, including integrin activation, aggregation, and thrombus formation. A mechanistic link was also found between PKM2 and PI3K-mediated Akt/GSK3 signaling in platelets. It was speculated that PMK2 regulates multiple aspects of platelet function via PI3 kinase-mediated Akt/GSK3 signaling, most likely through glycerophospholipid metabolism, for the following reasons. First, glycerophospholipid metabolism is known to be associated with PI3K-Akt mediated signaling that potentiates platelet activation. Second, PI3K-mediated signaling regulates GPVI and GPCR-mediated "inside-out" signaling and integrin αIIbβ3-mediated "outside-in" signaling in platelets. In addition to its role as a metabolic enzyme, a non-metabolic phosphorylase activity specific to PKM2 has been implicated in several cell types. The possibility that PKM2 regulates various platelet functions via its non-metabolic activity cannot be ruled out.

To confirm the role of PKM2 in regulating multiple aspects of platelet function in vivo, platelet-specific PKM2-deficient mice were generated. Consistent with the inhibitor studies, genetic ablation of PKM2 inhibited lactate production in stimulated-platelets, concomitant with decreased integrin αIIbβ3 activation, P-selectin surface expression, platelet aggregation and clot retraction with multiple agonists, including GPVI and GPCR agonists. It was also found that the deletion of PKM2 in platelets down-regulated PI3K-mediated Akt/GSK3 signaling in platelets. Furthermore, platelet-specific PKM2-deficient mice or wild-type mice pretreated with ML265 were less susceptible to arterial thrombosis in two experimental models of arterial thrombosis. Interestingly, it was found that the effect of ML265 on arterial thrombosis was more pronounced (50% of mice did not occlude) than platelet-specific deficiency of PKM2 in mice. It is speculated that this might be due to the inhibitory effect of ML265 on dimeric PKM2 in cell types other platelets such as neutrophils and monocytes, which are known to exhibit a high rate of aerobic glycolysis. Neutrophils and monocytes are known to contribute to thrombus propagation through several mechanisms involving tissue factor, extracellular nuclear traps, and platelet-leukocyte aggregates. Despite having an effect on thrombosis, deletion of PKM2 in platelets did not affect tail bleeding time in mice suggesting a normal hemostatic response.

Figure 7:
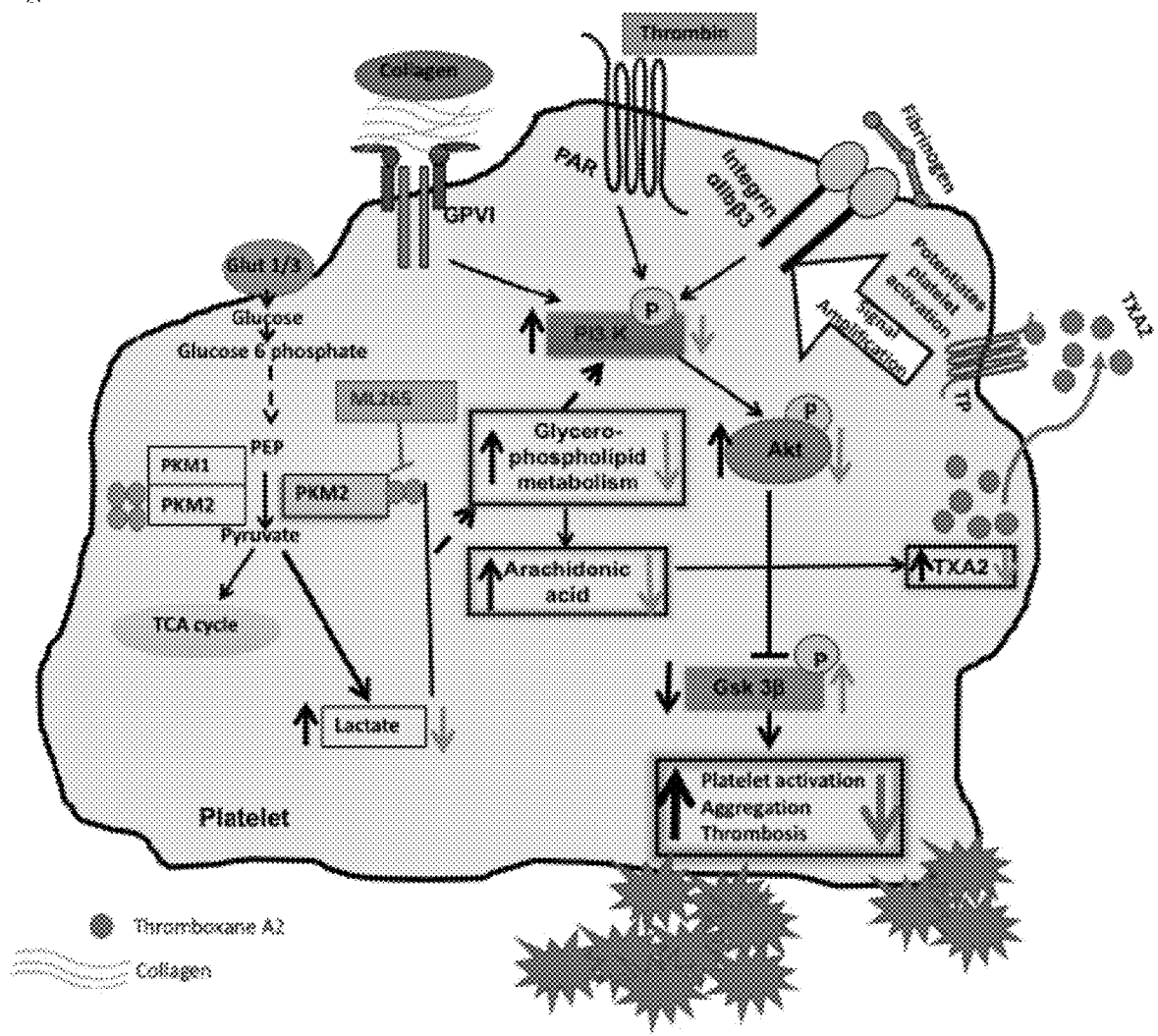
FIG. 7. Summary scheme illustration showing link between PKM2 mediated metabolism, cellular signaling, platelet function, and thrombosis. In the presence of excess glucose, dimeric PKM2 increases glucose uptake and lactate production, which results in metabolic reprogramming resulting in the upregulation of glycerophospholipid and arachidonic acid metabolites. Arachidonic acid is utilized for the synthesis of thromboxane A2, an endogenous agonist that further enhances platelet activation and aggregation via PI3 kinase-mediated Akt/GSK3β signaling to sub-maximal stimulus-response to GPVI (collagen and convulxin) and GPCR (ADP and thrombin). Abbreviations: PKM1, Pyruvate kinase M1; PKM2, Pyruvate kinase M2, Glut1, Glucose transporter 1; Glut3, Glucose transporter 3; GPVI, glycoprotein VI; ML265, small-molecule inhibitor of dimeric PKM2; PI3K (phosphatidylinositol 3-kinases); Akt (Protein kinase B or serine/threonine-specific protein kinase; Gsk3 b, glycogen synthase kinase 3 beta; TxA₂, thromboxane A2.

Platelet hyperactivation and thrombotic risk are associated with several pre-comorbid conditions, including obesity, hypertension, hyperlipidemia, atherosclerosis, and cancer. These pre-comorbid conditions often increase the risk of coronary artery disease or stroke. Current antiplatelet therapies are often effective in preventing primary or secondary coronary events in patients at high risk and safety remains a concern due to a significant risk of bleeding. A particular strength of the current study is the observation that therapeutic targeting with a single dose of the small molecule ML265 inhibited platelet aggregation in human and murine platelets, and potential experimental thrombosis formation in mice without having an effect on hemostasis. Notably, dimeric PKM2 expression is elevated in monocytes and macrophages from patients with coronary artery disease. Other studies have found that dimeric PKM2 is an activator of transcription of pro-inflammatory mediators, including IL-1β and IL-6 and a driver of M1 macrophage polarization. This suggests that PKM2 not only regulates thrombosis but also inflammation. This suggests that therapeutically targeting dimeric PKM2 may be beneficial in patients at risk for coronary artery diseases. In summary, we have uncovered a novel regulatory pathway in platelets, that coordinates multiple aspects of platelet function, from metabolic plasticity to cellular signaling to thrombosis (FIG. 7).

Mice and Human Subjects

Mice

Male and female mice on C57BL/6J background, used in the present study were 3 to 4 weeks (14-16 or 8 to 10 weeks (22-28 g) old mice. Platelets for infusion were isolated from 4- to 6-month old donor mice of the same genotype. The University of Iowa Animal Care and Use Committee approved all experiments. In vivo studies were performed according to the current Animal Research: Reporting of In Vivo Experiment guidelines).

Human Subjects

Human venous blood was drawn from healthy donors in accordance with the Declaration of Helsinki and approved by the Institutional Review Board (IRB), University of Iowa. All participants gave written informed consent.

Methods Details

Human Platelet Isolation

To obtain human platelets, blood was collected from healthy volunteers free from antiplatelet medication. Informed consent was taken. Platelets were prepared as described. Briefly, blood was collected in tubes containing anticoagulant citrate dextrose solution A and centrifuged at 180 g for 20 min. After addition of apyrase (0.6 U/ml) to PRP, platelets were sedimented by centrifugation at 800 g for 15 min. Cells were washed in buffer A (20 mM HEPES, 138 mM NaCl, 2.9 mM KCl, 1 mM MgCl2, 0.36 mM NaH2PO4, 1 mM EGTA (ethylene glycol tetraacetic acid), supplemented with 5 mM glucose, pH 6.2). Platelets were finally resuspended in buffer B (pH 7.4), which was the same as buffer 'A' but without EGTA and apyrase.

Mouse Platelet Isolation

Mouse platelets were prepared. Blood from anesthetized mice was drawn from the retro-orbital plexus and collected in 1.5 mL polypropylene tubes containing 300 µL of enoxaparin (0.3 mg/mL; Sanofi-Aventis, US LLC). The blood was centrifuged at 100 g for 5 minutes, and the platelet-rich plasma (PRP) was collected in a fresh tube. To prevent platelet activation, PRP was incubated with $PGI_2$ (2 µg/mL) at 37° C. for 5 minutes. PRP was further centrifuged at 600 g for 5 minutes. The obtained pellets were suspended in 1 mL modified Tyrode-N-2-hydroxyethylpiperazine-N'-2-ethane sulfonic acid (HEPES) buffer (137 mM NaCl, 0.3 mM $Na_2HPO_4$, 2 mM KCl, 12 mM $NaHCO_3$, 5 mM N-2-hydroxyethylpiperazine-N'-2-ethane sulfonic acid, 5 mM glucose, 0.35% bovine serum albumin, pH 7.2). The washing step was repeated twice with Tyrode's to remove $PGI_2$, and platelets were fluorescently labeled with calcein green (wherever required), AM (2.5 µg/mL; Molecular Probes) for 10 minutes at 37° C.

Sample Preparation for Metabolomic Study

Human washed platelets ($3 \times 10^8$ cells in 300 µl) were treated with ML265 (100 µM) or DMSO for 10 mins and stimulated by convulxin for 10 minutes. Cells were then fixed by adding 80% methanol and sent to Metabolon Inc. (Morrisville, NC, USA) for metabolomic analysis. Briefly, samples were homogenized and subjected to methanol extraction then split into aliquots for analysis by ultra-high-performance liquid chromatography/mass spectrometry (UHPLC/MS) in the positive (two methods) and negative (two methods) mode. Metabolites were then identified by automated comparison of ion features to a reference library of chemical standards followed by visual inspection for quality control as previously described (Dehaven et al., 2010). Metaboanalyst 4.0 feature PatternHunter was used for finding the metabolites showing correlation (≥0.5) with specific trends (Xia et al., 2009). The metabolites obtained after PatternHunter analysis have been represented as a heatmap. Furthermore, to understand the functional role of the changes in concentration of these metabolites, the pathway analysis was performed using Metaboanalyst 4.0. The Global Ancova and Relative-betweenness Centrality topological measures were used to identify the highly impacted pathways with KEGG human metabolic library as the reference. The False Discovery Rate corrected pathway terms with P≤0.05 were considered significant.

Glucose Uptake Assay

Glucose uptake was determined in activated versus non-activated platelets using 10 mM $^{14}$C-2-deoxy-glucose. Washed platelets ($2 \times 10^8$/mL) treated with vehicle (DMSO) or ML265 (50 and 100 µM) were incubated in 1× Tyrode buffer and stimulated with convulxin or thrombin for 10 minutes, placed on ice and then centrifuged at 4000 rpm for 5 minutes. The pellets were washed with cold 1×PBS and solubilized in 1N NAOH. Radioactive counts were determined using a Perkin Elmer TriCarb 2800TR liquid scintillation counter.

Lactate Measurement

Washed platelets ($5 \times 10^8$ platelets/mL) in DMEM (5 mM HEPES, 25 mM glucose, 1 mM pyruvate and 2 mM glutamine) were pre-treated with 50 or 100 µM of ML265 or vehicle (DMSO) for 10 mins and stimulated by convulxin (200 ng/ml) for 1 hr. Cells were centrifuged and supernatant was collected. Levels of L-lactate in supernatant were determined using a glycolysis cell based assay kit (Cayman; Item No. 600450) according to the manufacturer's instructions.

Thromboxane ($TxB_2$) Assay

The $TxB_2$ assay was done. Briefly, PRP or washed platelets ($2 \times 10^8$ platelets/mL) was stimulated with convulxin or thrombin for 3 minutes utilizing an aggregometer, and the reaction was stopped by quickly freezing the sample in a dry ice-methanol bath. Before performing the TXB2 measurement assay, samples were thawed and centrifuged at 15,000 g for 3 minutes. The supernatants were diluted 1:50 with assay buffer and levels of $TxB_2$ (a stable metabolite of $TxA_2$) were determined in triplicate using an immunoassay kit (Abcam Thromboxane B2 enzyme-linked immunosorbent assay kit) according to the manufacturer's instructions.

In Vitro Platelet Aggregation and ATP Secretion

Platelet rich plasma (PRP) or washed platelets ($2 \times 10^8$/ml) treated with vehicle (DMSO) or ML265 (50 and 100 µM) were stirred (1200 rpm) at 37° C. for 2 min in a whole blood/optical lumi-aggregometer (Chrono-log; model 700-2) before the addition of agonists (convulxin, collagen, thrombin, PAR4, TRAP (PAR1 agonist) or adenosine diphosphate [ADP]). Aggregation was measured as percent change in light transmission, where 100% refers to transmittance through the blank sample (PRP/Buffer). Platelet dense granule secretion was determined by measuring the release of ATP using luciferin-luciferase reagent. To examine the effect of ML265 on ATP secretion, washed platelets were pretreated with vehicle (DMSO) or ML265 (50 and 100 μM) for 10 minutes before stimulation with various agonists. ATP release was performed in a lumi-aggregometer (Chrono-log; model 700-2) at 37° C.

P-Selectin Expression

Platelets ($1 \times 10^8$ cells in 100 μl) were pre-incubated for 10 min either in presence or absence of ML265 (50 and 100 μM) then stimulated by convulxin or TRAP without stirring. Following this, platelets were labeled with PE-labeled anti-CD61 antibody and FITC conjugated anti-CD62P antibody. The platelet samples were incubated for 30 min in the dark at room temperature and analyzed on the flow cytometer (FACS Calibur, Becton Dickinson). An amorphous region (gate) was drawn to differentiate the platelets from the noise and multi-platelet particles. After compensation for FITC and PE, CD61-positive 10,000 events were collected for each sample.

Annexin V-Affinity Assay

Mouse and human washed platelets ($1 \times 10^8$/ml) were pre-incubated with different concentrations of ML265 (10, 25, 50, 150, 200 and 300 mM). Washed platelets activated with thrombin (0.5 U/ml)+convulxin (100 ng/ml) were used as a positive control. The samples were added to 1× Annexin V-binding buffer (BD Biosciences). Following this, annexin V-FITC antibody was added to each sample, gently mixed, and incubated at room temperature for 15 minutes in the dark. After incubation, 1× Annexin-binding buffer was added to each tube and analyzed by a Becton Dickinson FACSCalibur flow cytometer.

Clot Retraction

To measure thrombin-stimulated fibrin clot retraction PRP was treated with ML265 (50 and 100 μM) or vehicle control (DMSO) for 10 minutes. Tyrode buffer was added to test tubes, along with red blood cells, to allow visualization of the clot. This was followed by the addition of PRP. Clot formation was initiated by adding thrombin (final concentration 0.25 U/ml) to the test tubes. Photographs were taken every 15 minutes and the assay was terminated after 60 minutes at which time the clot in the vehicle-treated samples were seen to have retracted completely. Clot area was analyzed using Image J software from NIH (Bethesda, MD, USA).

Bioflux Flow Chamber Assay

In vitro thrombosis assays were performed using Bio-Flux™ 200 (Fluxion Biosciences, USA) microfluidics flow chamber (Nayak et al., 2018). The channels were coated with Type I collagen (100 μg/ml) for one hour at room temperature and then blocked with 0.5% BSA for 30 minutes. Platelets were isolated from citrated whole blood as described above, washed, labeled with the fluorescent dye (calcein AM; 2 μM) and were reconstituted back with PPP and remaining blood containing leukocytes and RBC. The whole blood pretreated with ML265 or vehicle (DMSO) was perfused over the collagen-coated plate at shear stress 1500 $s^{-1}$ for 5 minutes. Experiments were performed in triplicates using whole blood from human and mice. The fluorescently labeled platelets/thrombi on the collagen-coated surface were analyzed using ImageJ software from NIH (Bethesda, MD, USA).

ML265 Preparation and Administration for In Vivo Experiments

Initially ML265 dissolved in DMSO was mixed with 200 μl of deionized water and administered intra-peritoneally to the at a dose of 25 and 50-mg/Kg body weight. In vivo thrombosis and tail transection assays were performed 10 minutes after administration of ML265 or vehicle infusion by a person who was blinded to the drug and vehicle infusion.

$FeCl_3$ Injury-Induced Carotid Thrombosis

Thrombus formation in the carotid artery after the $FeCl_3$ injury was assessed by intravital microscopy. Briefly, 8-10 weeks old mice were anesthetized using 100-mg/kg ketamine and 10-mg/kg xylazine. Platelets labeled with calcein green ($2.5 \times 10^9$ platelets per kg) were infused through the retro-orbital plexus. The common carotid artery was carefully exposed and kept moist by super-fusion with warm (~37° C.) saline. Whatman paper (0.5×1.5 mm) saturated with ferric chloride (5%) solution was applied topically for 1.5 minutes for male and 2 mins for female mice, and thrombus formation in the injured carotid vessel was monitored in real time using a Nikon upright microscope (Plan Fluor 4×/0.2 objective), and thrombus growth overtime was recorded using a high-speed electron-multiplying camera for 40 minutes or until occlusion occurred. The time to form occlusive thrombus was considered as the time required for blood to stop flowing completely for >1 minute. Videos were evaluated off-line using a Nikon computer-assisted image analysis program.

Laser Injury-Induced Mesenteric Artery Thrombosis

Micropoint laser ablation system (Andor technology) was used to make injury in the mesenteric arterioles. Briefly, young mice [3- to 4-weeks (14-16 gm) old male)] were used to minimize fat surrounding the arterioles and facilitate focusing of the laser. Fluorescent platelets labeled with calcein green ($1.5 \times 10^9$ platelets $kg^{-1}$) were infused in anesthetized mice through the retro-orbital plexus. Infused platelets were isolated from adult (4-5 months) donor mice of the same genotype. Mesenteric arterioles having a diameter of approximately 80-100 μm (with shear rates of ~1300-1800 $s^{-1}$) were used for the study. The specific illumination of the area of interest was carried out through the microscope eyepiece. The wavelength of light in the range of 365-400 nm with the maximum output of 50-500 uJ was used for illumination. The power and frequency of pulses were regulated by software and empirically defined. Thrombus growth in the injured vessel was monitored in real time by using a Nikon upright microscope with a Plan Fluor 10×/0.3 objective, and thrombus formation overtime was recorded using a high-speed EM camera for 3-4 min. In our experimental setup with the laser injury model, the thrombus grows to its maximum size in approximately 1 min, and then gradually disintegrates over time. Videos were evaluated and mean fluorescence intensity was calculated using a Nikon computer-assisted image analysis program.

Tail Bleeding Assay

Tail-transection bleeding time was measured. Briefly, mice (approximately 8 weeks of age) were anesthetized with 100-mg/kg ketamine and 10-mg/kg xylazine and placed on a heating pad warmed at 37° C., and a 3 mm segment of the tail was amputated with a sharp scalpel blade. The tail was immediately immersed in saline (at 37° C.), and the time taken for the stream of blood to stop for more than 30 seconds was defined as the bleeding time. If bleeding did not stop within 10 minutes, hemostasis was achieved by cauterizing the tail.

Immunoblotting

Platelet proteins were separated on 4-20% SDS-PAGE (sodium dodecyl sulfate-polyacrylamide gel electrophoresis) gradient gels and electrophoretic transferred to PVDF (polyvinylidene fluoride) membrane by using Bio-Rad western blotting system. For PKM2 dimer and tetramer study 6% native gels are used. Membranes were blocked with 5% BSA or skimmed milk in 10 mM Tris-HCl, 150 mM NaCl, pH 8.0 (TBS) containing 0.05% Tween-20 for one hour at room temperature. Blots were incubated for overnight with primary antibody, followed by horseradish peroxidase-labeled secondary antibody for one hour. Blots were developed using enhanced chemiluminescence and quantified using Image J software from NIH (Bethesda, MD, USA).

Quantification and Statistical Analysis

Statistical Analysis

Statistical analysis (numbers, averages, deviation, and statistical tests) are reported in the figures and corresponding legends, performed in GraphPad Prism. Data are represented as mean±standard error (SEM) in all the figures. For statistical analysis, GraphPad Prism software, version 8 was used. Shapiro-Wilk test and Brown-Forsythe test was done for normality and variance, respectively. The statistical significance was assessed using either unpaired t-test or one-way ANOVA followed by Tukey's or Holm-Sidak's multiple comparisons test (for normally distributed data) and Mann Whitney test or Kruskal-Wallis test followed by Dunn's multiple comparisons test (for not normally distributed data). P<0.05 was considered to be statistically significant. Number of samples for all experiments were chosen based on standard experimental practice in the field.

Example 2

ML265 Inhibits Platelet Aggregation and Arterial Thrombosis in Pre-Existing Comorbid Condition of Obesity Experiments were performed that determined that ML265 inhibited platelet aggregation and arterial thrombosis in pre-existing comorbid condition of obesity. The results of the experiments are provided in FIGS. 16A-16D.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of inhibiting thrombosis without altering hemostasis by administering a composition comprising an inhibitor of dimeric pyruvate kinase M2 (PKM2) or an activator/stabilizer of tetramer PKM2 in a patient in need thereof,
   wherein the dimeric PKM2 inhibitor or activator/stabilizer of tetramer PKM2 is ML265; and
   wherein the administration of the composition does not alter hemostasis in the patient.

2. The method of claim 1, wherein the thrombosis is inhibited by the PKM2 inhibitor by more than about 10%.

3. The method of claim 1, wherein the thrombosis is inhibited by the PKM2 inhibitor by more than about 60%.

4. The method of claim 1, wherein the administration is by oral administration, intravenous infusion, or intraperitoneal administration.

5. The method of claim 1, wherein the composition is formulated for extended release.

* * * * *